US008834895B2

(12) United States Patent
Chen et al.

(10) Patent No.: US 8,834,895 B2
(45) Date of Patent: Sep. 16, 2014

(54) **USE OF *FRANCISELLA TULARENSIS* FOR PREVENTION AND TREATMENT OF ALLERGIC AIRWAY DISORDERS**

(75) Inventors: Wangxue Chen, Nepean (CA); Girishchandra Babubhai Patel, Nepean (CA)

(73) Assignee: National Research Council of Canada, Ottawa, Ontario (CA)

( * ) Notice: Subject to any disclaimer, the term of this patent is extended or adjusted under 35 U.S.C. 154(b) by 532 days.

(21) Appl. No.: 12/529,678

(22) PCT Filed: Mar. 20, 2008

(86) PCT No.: PCT/CA2008/000542
§ 371 (c)(1),
(2), (4) Date: Jan. 21, 2010

(87) PCT Pub. No.: WO2008/113183
PCT Pub. Date: Sep. 25, 2008

(65) Prior Publication Data
US 2011/0002854 A1    Jan. 6, 2011

Related U.S. Application Data

(60) Provisional application No. 60/896,156, filed on Mar. 21, 2007.

(51) Int. Cl.
*A61K 39/02* (2006.01)
*A61K 39/00* (2006.01)
*A61K 9/00* (2006.01)

(52) U.S. Cl.
CPC ......... *A61K 39/0208* (2013.01); *A61K 2039/58* (2013.01); *A61K 9/0073* (2013.01); *A61K 2039/522* (2013.01); *A61K 9/0043* (2013.01); *A61K 2039/543* (2013.01)
USPC .......................... 424/234.1; 530/412; 530/418

(58) Field of Classification Search
None
See application file for complete search history.

(56) References Cited

U.S. PATENT DOCUMENTS

2004/0022793 A1    2/2004 Severn et al.

OTHER PUBLICATIONS

Greenspan et al (Nature Biotechnology 7: 936-937, 1999.*
Chothia et al (The EMBO Journal, 1986, 5/4:823-26).*
Sandstrom et al (Infect. Immun. Jul. 1984. 45(1): 101-106).*
Koskela et al (Infect. Immun. Jun. 1982. 36(3): 983-989).*
Conlan, J.W. et al.; Aerosol-, but not intradermal-immunization with the live vaccine strain of *Francisella tularensis* protects mice against subsequent aerosol challenge with a highly virulent type A strain of the pathogen by an T cell- and interferon gamma-dependent mechanism; Vaccine; 2005; vol. 23; pp. 2477-2485.
Erb, K.J. et al.; Infection of mice with *Mycobacterium bovis*-Bacillus Calmette-Guerin (BCG) Suppresses Allergen-induced Airway Eosinophilia; J. Exp. Med.; 1998; vol. 187; No. 4; pp. 561-569.
Hansen, G. et al.; Vaccination with Heat-Killed Listeria as Adjuvant Reverses Established Allergen-Induced Airway Hyperreactivity and Inflammation: Role of CD8+ T cells and IL-181; J. Immunol; 2000; vol. 164; pp. 223-230.
Kuolee, R. et al.; Inhibition of airway eosinophilia and pulmonary pathology in a mouse model of allergic asthma by the live vaccine strain of *Francisella tularensis*; Clin. Exp. Allergy; epublished Feb. 26, 2008.
Fulop, M. et al.; Role of two outer membrane antigens in the induction of protective immunity against *Francisella tularensis* strains of different virulence; FEMS Immunology and Medical Microbiology; 1996; vol. 13; pp. 245-247.
Koskela, P. et al.; Cell-Mediated and Humoral Immunity Induced by a Live *Francisella tularensis* Vaccine; Infection and Immunity; Jun. 1982; pp. 983-989.
Ennis, Darren P. et al.; Whole-Cell Pertusis Vaccine Protects Against *Bordetella pertussis* Exacerbation of Allergic Asthma; Immunology Letters; 2005; vol. 97; pp. 91-100.
Ennis, D.P. et al.; Prior *Bordetella pertussis* Infection Modulates Allergen Priming and the Severity of Airway Pathology in a Murine Model of Allergic Asthma; Clinical and Experimental Allergy; 2004; vol. 34; pp. 1488-1497.
Young-Suk, Kim et al.; Inhibition of Murine Allergic Airway Disease by *Bordetella pertussis*; Immunology; 2004; vol. 112; pp. 624-630.
Feleszko, Wojciech et al.; Toll-Like Receptors-Novel Targets in Allergic Airway Disease (Probiotics, Friends and Relatives); European Journal of Pharmacology; 2006; vol. 533; pp. 308-318.
Matricardi, P.M. et al.; Microbial Products in Allergy Prevention Therapy; Allergy; 2003; vol. 58; pp. 461-471.
Renz, H. et al.; The Bidirectional Capacity of Bacterial Antigens to Modulate Allergy and Asthma; European Respiratory Journal; 2002; vol. 19; pp. 157-171.
Chen, Wangxue et al.; Interleukin 1: An Important Mediator of Host Resistance Against *Pneumocytis carinii*; J. Exp. Med.; Sep. 1, 1992; vol. 176; pp. 713-718; Rockefeller University Press.
Cho, S.-H. et al.; Peripheral Blood CD4+ and CD8+ T Cell Type 1 and Type 2 Cytokine Production in Atopic Asthmatic and Normal Subjects; Clin Exp All; 2002; vol. 32; pp. 427-433; Blackwell Science Ltd.
Cembrzynska-Nowak, Monika et al.; Elevated Release of Tumor Necrosis Factor-alpha and Interferon-gamma by Bronchoalveolar Leukocytes from Pateints with Bronchial Asthma; Am Rev Respir Dis; 1993; vol. 147; pp. 291-295.

(Continued)

*Primary Examiner* — Jennifer Graser
(74) *Attorney, Agent, or Firm* — Bennett Jones LLP

(57) ABSTRACT

A pharmaceutical composition for treating or preventing a Th2-mediated disease or disorder includes live, killed or attenuated *Franciscella tularensis* or its components. The *F. tularensis* cells may be LVS cells. Administration of an effective amount may prevent or reduce bronchoconstriction or allergic airway inflammation through a T-helper cell (Th) 1-mediated suppression of an ongoing Th2 response mechanism.

27 Claims, 10 Drawing Sheets

(56) References Cited

OTHER PUBLICATIONS

Chen, Wangzue et al.; *Helicobacter pylori* Infection; Inhibition of Mitogen-Induced Murine Lymphocyte Proliferation by *Heliobacter pylori* Cell-Free Extract; Journal of Gastroenterology and Hepatology; 2000; vol. 15; pp. 1000-1006; Blackwell Science Asia Pty. Ltd.

Conlan, J. Wayne et al.; Experimental Tularemia in Mice Challenged by Aerosol or Intradermally with Virulent Strains of *Francisella tularensis*: Bacteriologic and Histopathologic Studies; Science Direct; 2003; vol. 34; pp. 239-248; Elsevier Science Ltd.

Douwes, Jeroen et al.; Can Bacterial Endotoxin Exposure Reverse Atopy and Atopic Disease?; J. Allergy Clin Immunol; Nov. 2004; vol. 114; pp. 1051-1054; American Academy of Allergy, Asthma and Immunology.

Elias, Jack A. et al.; New Insights into the Pathogenesis of Asthma; J. Clin. Invest.; Feb. 2003; vol. 111, No. 3; pp. 291-293.

Eigelsbach, Henry T. et al.; Prophylactic Effectiveness of Live and Killed Tularemia Vaccines: I. Production of Vaccine and Evaluation in the White Mouse and Guinea Pig; J. Immunol.; 1961; vol. 87; pp. 415-425; The American Association of Immunologists, Inc.

Elkins, Karen L. et al.; Innate and Adaptive Immune Responses to an Intracellular Bacterium, *Francisella tularensis* Live Vaccine Strain; Science Direct; 2003; vol. 5; pp. 135-142; Elsevier SAS.

Rodriguez, Dunia et al.; Bacterial Lipopolysaccharide Signaling Through Toll-Like Receptor 4 Suppresses Asthma-Like Responses Via Nitric Oxide Synthase 2 Activity; J. Immunol.; 2003; vol. 171; pp. 1001-1008; The American Association of Immunologists, Inc.

Jain, Vipul V. et al.; Mucosal Immunotherapy with CpG Oligodeoxynucleotides Reverses a Murine Model of Chronic Asthma Induced by Repeated Antigen Exposure; Am J Physiol Lung Cell Mol Physiol; 2003; vol. 285; pp. L1137-L1146; The American Physiological Society.

Kline, Joel N. et al.; Treatment of Established Asthma in a Murine Model Using CpG Oligodexynucleotides; Am J Physiol Lung Cell Mol Physiol; 2002; vol. 283; pp. L170-L179; The American Physiological Society.

Lazaar, Aili L. et al.; Pathogenisis and Treatment of Asthma: Recent Advances; 2004; vol. 1, No. 1; pp. 111-115; Elsevier Ltd.

Livak, Kenneth J. et al.; Analysis of Relative Gene Expression Data Using Real-Time Quantitative PCR and the 2-CT Method; Meth; 2001; vol. 1262; pp. 402-408; Elsevier Science (USA).

Lukacs, Nicholas W.; Role of Chemokines in the Pathogensis of Asthma; Immunol; 2001; vol. 1; pp. 108-116; Macmillan Magazines Ltd.

Major Jr., Tamas et al.; Application of Heat Killed *Mycobacterium bovis*-BCG into the Ling Inhibits the Development of Allergen-Induced Th2 Responses; Vaccine; 2002; vol. 20; pp. 1532-1540; Elsevier Science Ltd.

Patel, Girishchandra B. et al.; Archaeosomes as Adjuvants for Combination Vaccines; Journal of Liposome Research; 2004; vol. 14, Nos. 3 and 4; pp. 191-202; Marcel Dekker, Inc.

Larsson, Par et al.; The Complete Genome Sequence of *Francisella tularensis*, the Causative Agent of Tularemia; Nature genetics; 2005; vol. 37, No. 2; pp. 153-159.

Schwarze, Jurgen et al.; Respiratory Syncytial Virus Infection Results in Airway Hyperresponsiveness and Enhanced Airway Sensitization of Allergen; J. Clin. Invest.; Jul. 1997; vol. 100, No. 1; pp. 226-233; The American Society for Clinical Investigation, Inc.

Smit, Joost J. et al.; Therapeutic Treatment with Heat-Killed *Mycobacterium vaccae* (SRL172) in a Mild and Severe Mouse Model for Allergic Asthma; European Journal of Pharmacology; 2003; vol. 470; pp. 193-199; Science Direct.

Sayers, Ian et al.; Suppression of Allergic Airway Disease Using Mycobacterial Lipoglycans; J Allergy Clin Immunol; 2004; vol. 114; pp. 302-309; American Academy of Allergy, Asthma and Immunology.

Strachan, David P.; Hay Fever, Hygiene, and Household Size; Br Med J; 1989; vol. 299; pp. 1259-1260.

Tarnvik, Arne; Nature of Protective Immunity to *Francisella tularensis*; Reviews of Infectious Diseases; 1989; vol. 11, No. 3; pp. 440-451; Oxford University Press.

Weinberger, Miles; Respiratory Infections and Asthma: Current Treatment Strategies; Drug Discovery Today; Oct. 2004; vol. 9, No. 19; pp. 831-837; Elsevier Ltd.

Andersson, Henrik et al.; Transcriptional Profiling of Host Responses in Mouse Lungs Following Aerosol Infection with Type A *Francisella tularensis*; Journal of Medical Microbiology; 2006; vol. 55; pp. 263-271; SGM Journals.

Vinogradov, Evgeny et al.; Structural Analysis of *Francisella tularensis* Lipolysaccharide; Eur. J. Biochem; 2002; vol. 269; pp. 6112-6118; FEBS.

Wohlleben, Gisela et al.; Influenza A Virus Infection Inhibits the Efficient Recruitment of Th2 Cells into the Airways and the Development of Airway Eosinophilia; J. Immunol.; 2003; vol. 170; pp. 4601-4611; The American Association of Immunologists, Inc.

Kline, Joel N. et al.; Cutting Edge: Modulation of Airway Inflammation by CpG Oligodeoxynucleotides in a Murine Model of Asthma; J. Immunol; 1998; vol. 160; pp. 2555-2559; The American Association of Immunologists, Inc.

European Patent Office; Application No. 08 733 646.7; Office Action dated Apr. 17, 2012.

European Patent Office; Application No. 08 733 646.7; Extended European Search Report dated Mar. 2, 2010.

* cited by examiner

USE OF *FRANCISELLA TULARENSIS* FOR PREVENTION AND TREATMENT OF ALLERGIC AIRWAY DISORDERS

CROSS REFERENCE TO RELATED APPLICATIONS

This application claims the priority benefit of U.S. Provisional Patent Application No. 60/896,156 filed on Mar. 21, 2007 entitled "Use of *Francisella Tularensis* For Prevention and Treatment Of Allergic Airway Disorders".

FIELD OF THE INVENTION

The present invention relates to the use of *Francisella tularensis* or components in the prevention or treatment of allergic airway disorders.

BACKGROUND OF THE INVENTION

Allergic asthma is a chronic respiratory disease characterized by airway inflammation, excessive mucus production, reversible airway obstruction, and airway hyperreactivity (AHR) (Lazaar and Panettieri, 2004). The aetiopathogenesis of allergic asthma is complex and encompasses the interplay between genetic predisposition, environmental triggers and dysregulated immune response (Lazaar and Panettieri, 2004, Lukacs, 2001). The precise mechanism of chronic airway inflammation that characterizes persistent asthma remains elusive, but appears to result from a strongly allergen-driven type 2-skewed $CD4^+$ T helper (Th2) lymphocyte infiltration of the airways with the induction of Th2 cytokines interleukin (IL)-4, IL-5, IL-13 and IL-25 (Lazaar and Panettieri, 2004). These cytokines function in concert with CC chemokines (such as eotaxins and thymus and activation-regulated chemokines) and, to a lesser extent, CXC chemokines and result in the recruitment and activation of eosinophils and IgE production (Lazaar and Panettieri, 2004, Lukacs, 2001). Infiltration of eosinophils and other inflammatory cells in the lower respiratory tract is the hallmark of allergic asthma, and may be important in the pathogenesis of this disease (Lazaar and Panettieri, 2004, Lukacs, 2001). Besides allergic asthma, there are many other diseases and disorders that are thought to be caused or exacerbated by the elicitation of Th2 skewed immune responses. Some examples of such disorders and diseases are atopic disorders, pulmonary eosinophilia, eczema, dermatitis, and allergic rhinitis.

Asthma affects approximately 8-10% of the US population, is the leading cause of hospitalization among children less than 15 years of age, and costs society billions of dollars annually (Elias et al., 2003). Despite its public health and economic significance, there are relatively few novel therapies and strategies with proven efficacies available for clinical management of asthmatic patients (Lazaar and Panettieri, 2004, Weinberger, 2004). Although current standard therapies, inhaled bronchodilators ($\beta_2$ receptor agonists) and anti-inflammatory drugs (corticosteroids), provide effective symptomatic control for the majority of asthma patients, they are sometimes accompanied by certain side effects, particularly in children and in patients with severe asthma requiring high-dose treatments (Lazaar and Panettieri, 2004). Moreover, these therapies require long-term daily administration, and they do not target the underlying immune mechanisms causing allergic asthma (Lazaar and Panettieri, 2004).

The rapid increase in asthma incidence in both the developed and developing countries over the past few decades, suggests that certain environmental, in addition to genetic, factors may contribute to the development of allergic asthma (Strachan, 1989). In this regard, increasing epidemiological and clinical data have suggested that a lack of early childhood exposure to microbial stimulation could favor the development of allergic diseases in genetically predisposed individuals (hygiene hypothesis) (Strachan, 1989). As asthma and allergic airway diseases are disorders associated with a predominant Th2 immune response, suppression of the aberrant allergen-specific Th2 response through antagonism or the induction of regulatory T cells by certain microbes and their products, particularly during neonatal and early childhood periods, may shift the immune response towards a Th1 phenotype and thereby prevent the development of and/or alleviate the clinical symptoms of allergic airway disease (Erb et al., 1998, Hansen et al., 2000, Kline et al., 2002, Matricardi et al., 2003). Indeed, recent experimental and clinical studies have supported the notion that immunization with certain microbes and their products can reduce asthma-like responses (Ennis et al., 2005, Erb et al., 1998, Hansen et al., 2000, Jain et al., 2003, Kim et al., 2004, Kline et al., 2002, Matricardi et al., 2003, Rodriguez et al., 2003, Sayers et al., 2004, Smit et al., 2003, Wohlleben et al., 2003). However, not all microbe-elicited Th1-biased host responses can alleviate the asthma-like symptoms (Schwarze et al., 1997), and some (e.g. *Bordetella pertussis*, respiratory syncytial virus) may exacerbate airway hyperresponsiveness under certain circumstances (Ennis et al., 2004). On the other hand, systemic immunization with heat-killed whole-cell *B. pertussis* inhibits allergic airway reactions (airway eosinophilia, lung inflammation and airway hyperresponsiveness)(Kim et al., 2004), despite the fact that both *B. pertussis* infection and immunization with heat-killed *B. pertussis* cells induce Th1 immune response (Ennis et al., 2004, Kim et al., 2004). Hence, it is impossible to rationally predict the potential effect of different Th1 response-eliciting microbes and their components on the allergic airway disease. Research results to date have led to suggestions that inhibition of airway eosinophilia maybe limited to mycobacterial infections which induce strong and sustained IFN-γ responses in the lungs (Erb et al., 1998). In the case of the use of *M. bovis* BCG in suppression of airway eosinophilia, an intranasal (i.n.) dose of $2\times10^3$ cfu was ineffective and a dose of $2\times10^5$ appeared to be optimal (Erb et al., 1998). However, mycobacterial infections involve a wider array of complex interactions involving proteins, unmethylated DNA, and cell wall components such as lipoglycans, phosphatidylinositol mannan (PIM) and lipoarabinomannan (LAM), which can modulate the host immune responses (Sayers et al., 2004). The use of molecules such as PIM isolated from organisms such as mycobacteria have been described for applications in alleviating Th2-mediated disorders/diseases (Severn et al., 2002). Additionally, heat-killed mycobacteria also suppress allergic airway disease (Sayers et al., 2004). The role of IFN-γ in suppression of airway hyperresponsiveness is confounded by the observation that the IFN-γ levels in asthmatic patients was in fact higher than in the normal cohorts (Cembrzynska-Nowak et al., 1993, Cho et al., 2002). The effect of mycobacterial infections on IgE and IgG1 isotype switching is not clear and contradictory, since some reports indicate that this occurs, whereas others show that it does not (Erb et al., 1998, Matricardi et al., 2003, Sayers et al., 2004). Although previous studies have demonstrated the ability of a number of microbes, including mycobacterial infections, and their products to modulate the course of allergic asthma in the mouse model, many of these treatments were only successful if initiated prior to OVA sensitization or immediately before airway challenge (Erb et al., 1998, Kim et al., 2004, Major et al., 2002).

SUMMARY OF THE INVENTION

*Francisella tularensis* is a gram-negative, facultative intracellular bacterium, and the causative agent of tularemia (Sjostedt and Brenner, 2002). The molecules LAM and PIM are not the constituents of *F. tularensis* cell walls (Larsson et al., 2005). The live vaccine strain (LVS) of *F. tularensis*, derived from a virulent type B strain of *F. tularensis* by passage on culture media (Eigelsbach and Downs, 1961), is attenuated for humans and does not cause chronic infection. LVS had been previously used as an investigational new drug and is currently approved for use in special immunization programs in the USA. LVS immunization induces strong local and systemic proinflammatory and Th1 cytokine responses in both human and murine vaccinees (Elkins et al., 2003, Tarnvik, 1989).

As described herein, live and killed LVS cells, and cell free extract components of LVS demonstrate suppression of the development of airway eosinophilia and associated pulmonary pathology in a mouse model of ovalbumin (OVA)-induced allergic asthma. Unexpectedly, we have found that LVS or cell free sonicate extract (CFSE) immunization or treatment was capable of inhibiting airway eosinophils, which is accepted as a hallmark of allegic airway disease, and its associated pulmonary pathology in mice that had already been sensitized to OVA. Accordingly, in one embodiment, the present invention exploits LVS and its components as prophylactic and therapeutic modalities for human allergic disorders.

In one aspect, the invention provides a pharmaceutical composition for the prevention or treatment of a Th2-mediated disease or a disorder in an animal, comprising live, killed or attenuated *Francisella tularensis* cells, or a cell-free sonicate extract of *Francisella tularensis* cells, or a fractional component of the cell-free sonicate extract of *Francisella tularensis* cells, and a pharmaceutically acceptable excipient, diluent or carrier. Preferably, the *Francisella tularensis* cells comprise LVS cells.

In one embodiment, the composition is formulated for topical, parenteral, intradermal or respiratory administration. In one embodiment, the composition is formulated into a dosage form selected from liquid dispersions, aerosols, gels, ointments or creams. Formulations for respiratory administration are preferred.

In one embodiment, the composition in unit dose form contains from about 100 cfu to about 200 cfu of live *Francisella tularensis* LVS per unit dose for respiratory administration.

In one embodiment, the composition in unit dose form contains about $10^6$ to about $10^8$ cells, and preferably about $10^7$ cells, of killed *Francisella tularensis* LVS per unit dose for respiratory administration.

In one embodiment, the composition in unit dose form contains about 50 µg to about 250 µg, and preferably about 150 µg, of cell-free sonicate extract per unit dose for respiratory administration.

In one embodiment, the composition in unit dose form contains about $10^4$ to about $10^6$, and preferably about $10^5$ cfu of live *Francisella tularensis* LVS cells per unit dose for intradermal or parenteral administration.

In one embodiment, the cell-free sonicate extract comprises a heat labile component.

In one embodiment, the fractional component comprises a protein or proteins obtainable by subjecting the cell-free sonicate extract to ion exchange chromatography using, for example, a Cellufine® sulfate ion exchange column and obtaining a protein complex which elutes after application of NaCl to the column, and which inhibits infiltration of eosinophils in the respiratory tract. In one embodiment, the protein complex comprises a precipitated protein fraction or a solubilized protein fraction, or both, obtainable by subjecting the eluted protein complex to de-salting. In one embodiment, the precipitated protein fraction and the solubilized protein fraction comprise moieties of molecular weight 50 kD or 60 kD, or both 50 kD and 60 kD.

In another aspect, the invention provides use of live, killed or attenuated *Francisella tularensis* cells, or a cell-free sonicate extract of *Francisella tularensis* cells, or a fractional component of the cell-free sonicate extract of *Francisella tularensis* cells in the prevention or treatment of a Th2-mediated disease or a disorder in an animal. Preferably, the *Francisella tularensis* cells are LVS cells.

In one embodiment, the Th2-mediated disease or disorder is selected from asthma, eczema, eosinophilic airway inflammation, airway hyperresponsiveness, allergic airway disease, dermatitis or a food allergy.

In one embodiment, the animal is a mammal selected from a mouse, dog, cat, sheep, goat, cow, horse, pig, non-human primate or human. In one embodiment, the mammal is a human.

In one embodiment, the live, killed or attenuated *Francisella tularensis* cells, the cell-free sonicate extract, or the fractional component is administered in the form of pharmaceutical composition described herein by topical, intradermal, parenteral or respiratory routes.

In yet another aspect, the invention provides use of live, killed or attenuated *Francisella tularensis* cells, or a cell-free sonicate extract of *Francisella tularensis* cells, or a fractional component of the cell-free sonicate extract of *Francisella tularensis* in the manufacture of a medicament for the prevention or treatment of a Th2-mediated disease or a disorder in an animal. In one embodiment, the medicament is manufactured in the form of the pharmaceutical compositions described herein for administration by topical, intradermal, parenteral or respiratory routes.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION OF PREFERRED EMBODIMENTS

Figure 1:
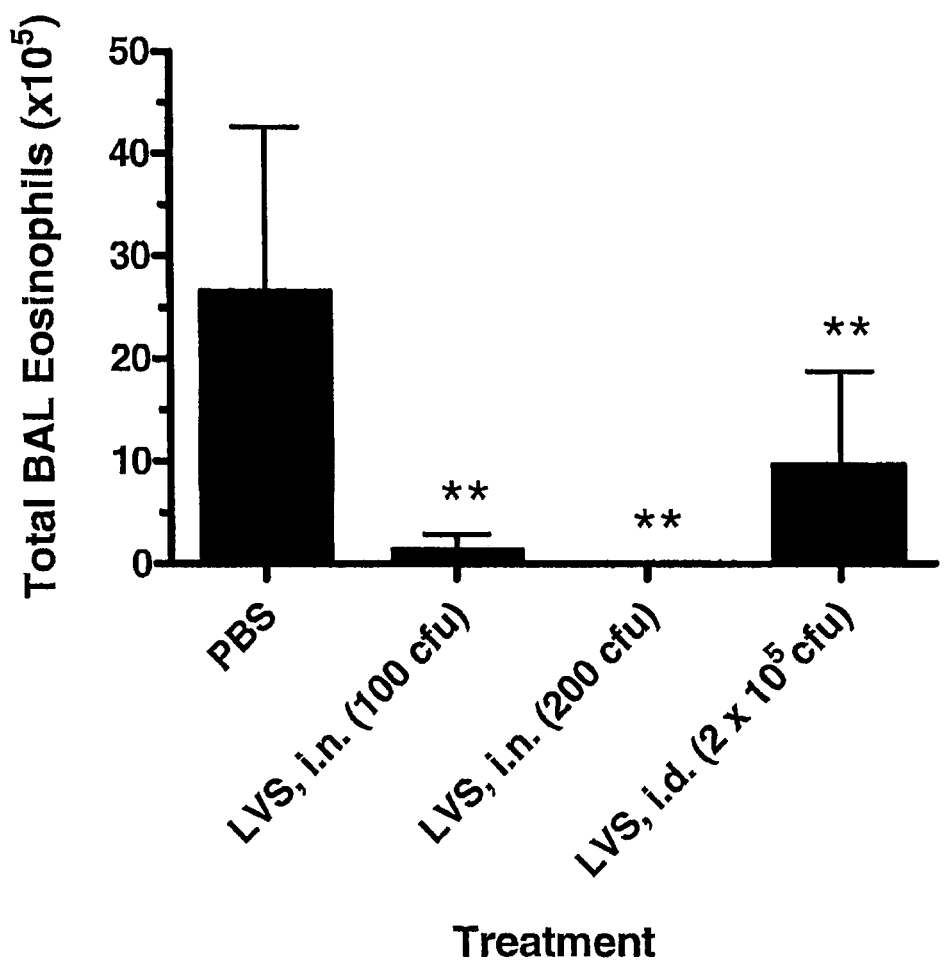
FIG. 1 is a graph showing the inhibition of airway eosinophilia in OVA sensitized mice by live *F. tularensis* LVS. Mice were sensitized i.p. with OVA/alum on days 0 and 14. Sensitized mice were treated with LVS or PBS by the indicated route on day 24, and intranasally challenged with OVA on day 45. Seven days after the i.n. OVA challenge, mice were euthanized and their lungs were lavaged. Total numbers of cells and the different cell types in the bronchoalveolar lavage (BAL) were enumerated on cytospin preparations. Each bar represents the mean total number of eosinophils in the BAL fluid ±SD (n=5 mice). The data presented are representative of 1 of at least 2 separate experiments with similar results. **$p<0.01$ compared to PBS-treated group.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

The applicants have discovered that the administration of *Francisella* tularensis, or components of *F. tularensis*, to a mouse sensitized to OVA inhibits eosinophilia when that mouse is later challenged with OVA. As a result, the applicants have conceived of an invention relating to methods of preventing or treating a Th2-mediated disease or a disorder in an animal, by administering a pharmaceutical composition comprising *F. tularensis* cells or its components and a pharmaceutically acceptable excipient, diluent or carrier.

The *F. tularensis* cells may be live, killed or attenuated. In one embodiment, the *F. tularensis* cells comprise LVS cells. The efficacy of the present invention has been demonstrated with whole cells, cell-free disrupted or sonicated extracts, or a fractional component thereof. Therefore, as used herein, "LVS or its components" or "*F. tularensis* or its components" may include live or killed cells, or a cell-free sonicate extract, or a fractional component of the cell-free sonicate extract. The LVS or its components need not include lipopolysaccharide (LPS) or any nucleic acids, as we have demonstrated that LPS or nucleic acids do not contribute to the efficacy of the present invention.

In one embodiment, a fractional component is obtainable by subjecting the cell-free sonicate extract to standard fractionation methods, such as ion exchange chromatography using, for example, a Cellufine® sulfate ion exchange column and obtaining a protein complex which elutes after application of NaCl to the column, and which inhibits infiltration of eosinophils in the respiratory tract. In one embodiment, the protein complex comprises a precipitated protein fraction or a solubilized protein fraction obtainable by subjecting the eluted protein complex to de-salting. In one embodiment, the precipitated protein fraction and/or the solubilized protein fraction comprise moieties of molecular weight 50 kD or 60 kD, or both 50 kD and 60 kD.

The Th2 mediated disease or disorder includes, without limitation, allergic airways diseases such as asthma and may also include other diseases or disorders such as atopic disorders, pulmonary eosinophilia, eczema, dermatitis, and allergic rhinitis.

Without being restricted to a theory, the applicants believe that *F. tularensis* cells or its components engage the immune system and shift the immune response towards a Th1 phenotype and thereby prevent the development of or alleviate the clinical symptoms of a Th2 mediated disease such as an allergic airway disease.

In one embodiment, a composition comprising LVS or its components is administered to a mammal susceptible to or suffering from a Th2 mediated disease or disorder. The LVS or its components may be administered in a physiologically acceptable diluent, carrier or vehicle, and may particularly be adapted for topical, intradermal, parenteral, or respiratory delivery. As used herein, "respiratory route" or "respiratory delivery" shall include intranasal, inhalation or insufflation delivery. Suitable carriers, vehicles, diluents, or excipients to create formulations suitable for such delivery methods are well known to those in the art, and need not be described herein.

For administration by intranasal formulation, the compositions of the present invention may be formulated as intranasal drops intended for use in the nares, as is well known in the art.

For administration by inhalation or insufflation, the compositions according to the invention are conveniently delivered by conventional means i.e. in the form of a metered dose inhaler prepared in a conventional manner or in combination with a spacer device, for example the Volumatic™ (Glaxo Group) device. In the case of a metered dose inhaler, a metering valve is provided to deliver a metered amount of the composition. Spray compositions may for example be formulated as aqueous solutions or suspensions and may be administered by a nebuliser. Aerosol spray formulations for example in which the active ingredients are suspended, optionally together with one or more stabilisers, in a propellant, e.g. a halogenated hydrocarbon such as trichlorofluoromethane, dichlorodifluoromethane, 1,2-dichlorotetrafluoroethane, trichlorotrifluoroethane, monochloropentafluoroethane, chloroform or methylene chloride may also be employed.

Alternatively, for administration by inhalation or insufflation, the compositions according to the invention may take the form of a dry powder composition, for example a powder mix of dried or freeze-dried LVS cells or its components, and a suitable carrier such as lactose. The powder compositions may be presented in unit dosage form in, for example, capsules, cartrides or blister packs from which the powder may be administered with the aid of an inhaler. Suitable inhalers may include the Rotahaler™ inhaler (Glaxo Group) or in the case of blister packs by means of the Diskhaler™ inhaler (Glaxo Group).

Representative animals include mammals such as mice, dogs, cats, sheep, goats, cows, horses, pigs, non-human primates, and humans. In a preferred embodiment, the mammal is a human.

The LVS or its components is administered in an amount sufficient to treat or prevent the Th2 mediated disease or disorder. The disease or disorder is treated when administration of the LVS or its components causes or mediates a clinically significant reduction in existing bronchoconstriction or inflammation, or both bronchoconstriction and inflammation. The disease or disorder is prevented if the administration of LVS or its components causes or mediates the absence, or a clinically significant reduction in severity of bronchoconstriction or inflammation, or both bronchoconstriction and inflammation. The dosages described herein derive from mouse model studies. One skilled in the art will know that an effective dosage will vary according to the body weight, method of delivery, and species of the animal being treated.

EXAMPLES

The following examples are intended to illustrate the present invention and describe certain embodiments, and should not be considered limiting of the claimed invention in any manner.

Example 1

Mice

Eight to 10 week-old specific-pathogen-free (SPF) female C57BL/6 and Balb/c mice were purchased from Charles River Laboratories (St Constant, Quebec). Mice were housed under SPF conditions in the Animal Facility, Institute for Biological Sciences, National Research Council Canada (Ottawa) and given free access to sterile water and ovalbumin (OVA)-free diet. The animals were maintained and used in accordance with the recommendations of the Canadian Council on Animal Care Guide to the Care and Use of Experimental Animals.

Example 2

*F. tularensis* LVS and Preparation of Cellular Components from *F. tularensis* LVS

*F. tularensis* LVS (ATCC 29684) stock culture was grown in modified Mueller-Hinton broth, harvested and aliquots of cells were frozen at −70° C. in the presence of 10% (w/v) sucrose (Conlan et al., 2003) for thawing and using as viable stock cell culture when required. The cell-free sonicate extract (CFSE) was prepared essentially in the same manner as that for *Helicobacter pylori* CFSE as described previously (Chen et al., 2000). Briefly, *F. tularensis* LVS stock culture was grown on cysteine heart agar supplemented with 1% (wt/vol) haemoglobin for 72 h at 37° C. The cells were harvested into sterile saline and disrupted by 5 minutes of sonication (30 s pulses at 60%, at 1 min intervals) on ice, using a Branson™ sonifier (model B15, Branson Sonic Power Company, Banbury, Conn., USA). The cells can alternately be disrupted using other means such as pressures extruders. Cell debris and unbroken cells were removed by centrifugation at 14 000×g for 20 min at 4° C. The supernatant was aliquoted and stored at −80° C. until use. The sterility of the CFSE was confirmed by plating on cysteine heart agar supplemented with 1% (w/v) haemoglobin, and its protein concentration was determined by the Bradford method (Bio-Rad Laboratories, Hercules, Calif., USA) using bovine serum albumin as the standard. In some experiments, CFSE was heated in a water bath at 55° C. for 60 min or at 100° C. for 30 min before use.

Purified *F. tularensis* LVS lipopolysaccharide (LPS) was kindly provided by Dr. Malcolm Perry (Vinogradov et al., 2002). *F. tularensis* LVS DNA was purified using QIAamp DNA Mini Kit (Qiagen Inc., Mississauga, Ontario).

Example 3

Induction of Airway Eosinophilia and LVS Immunization

Mice were sensitized by i.p. injection of 2 μg OVA (Sigma Chemical, Co., St. Louis, Mo.) in 100 1l of Imject Alum (Pierce Laboratories, Rockford, Ill.) on days 0 and 14 (hereafter referred to as sensitized or OVA-sensitized mice). On day 21 or thereafter, OVA-sensitized mice were intranasally challenged with 100 μg OVA in 50 μl of phosphate-buffered saline (PBS). Alternately, the OVA-sensitized mice were first treated/immunized with live LVS cells via intranasal (i.n.; 100 or 200 cfu in 50 μl of PBS) or intradermal (i.d.; 2×10$^5$ cfu in 50 μl of PBS) route, and were i.n. challenged with OVA after waiting for at least 21 more days in order to allow sufficient time for the mice to clear the LVS infection. Mice normally clear such an LVS infection by 15 days after administration (Conlan et al., 2003). In other experiments, sensitized mice were treated with heat-killed LVS (HK-LVS, equivalent to 10$^7$ cfu), 20 μg LPS from LVS, 150 μg CFSE (total protein basis), 10 μg *F. tularensis* LVS DNA or PBS in 50 μl volume, 7 days prior to the i.n. OVA challenge. Mice were anesthetized by i.p. injection of xylazine and ketamine for all i.n. treatments and challenges.

Example 4

Bronchoalveolar Lavage (BAL) and Histopathology

Mice were sacrificed by $CO_2$ asphyxiation 3 or 7 days after i.n. OVA challenge. Blood samples were collected by cardiac puncture, and sera separated and stored at −80° C. The trachea was then exposed through a midline incision and cannulated with a plastic catheter. The lungs were lavaged by instillation of five 1.0-ml aliquots of PBS supplemented with 3 mM EDTA (Chen et al., 1992). Total lavage cell numbers were counted on a haemocytometer, and differential cell counts were carried out on cytospin preparations stained with Hema3 Stain Set (Fisher Scientific, Middletown, Va.). BAL fluid was centrifuged at 3,000×g for 7 min, supernatants were removed and stored at −80° C. In some experiments, the lungs were removed immediately after lavage, fixed by immersion in 10% neutral buffered formalin, and processed by standard paraffin embedding methods (Department of Pathology and Laboratory Medicine, University of Ottawa, Ottawa). Sections were cut 4 μm thick, stained with haematoxylin-eosin (HE) and examined by light microscopy. In other experiments, the lungs from each mouse were minced into small pieces with scissors and homogenized in 2 ml of lysing buffer (300 mM $NaCl_2$, 15 mM Tris, 2 mM $MgCl_2$, and 2 mM Triton X-100, pH 7.4) supplemented with Complete® protease inhibitors (Roche Diagnostics Canada, Laval, Quebec). The supernatant was collected following centrifugation at 14 000×g and used for cytokine assays.

Example 5

ELISA Assays for OVA-Specific Immunoglobulin Isotypes

Serum OVA-specific IgG1 and IgG2a were measured using OVA-coated microtiter plates (Immulon 2, Thermo Labsystems, Franklin, Mass.) and detected using alkaline phosphatase conjugated goat anti-mouse IgG1 or anti-mouse IgG2a, respectively (Caltag Laboratories, Burlingame, Calif.), in conjunction with pNPP substrate (KPL, Inc., Gaithersburg, Md.)(Patel et al., 2004). Serum OVA-specific IgE was measured using anti-IgE mAb (4B-39, BD Biosciences, Mississauga, Ontario)—coated microtiter plates and detected using OVA-biotin/streptavidin—horseradish peroxidase (HRP) in conjunction with TMB substrate (KPL, Inc.)(Erb et al., 1998).

Example 6

Total RNA Isolation and Real-Time RT-PCR for Cytokine mRNA Expression

For cytokine mRNA study, groups of 5 mice were sacrificed at day 3 after i.n. OVA challenge and their lungs and tracheobronchial lymph nodes (TBLNs, the major draining lymph nodes of the lungs) were removed and immersed immediately in RNAlater® (Qiagen). Total RNA was isolated using the TRIzol® reagent (Invitrogen, Carlsbad, Calif.). RNA quality was confirmed by running 300 ng of each sample on a 1% agarose gel. RNA was then reverse transcribed into cDNA using GeneAmp Gold RNA PCR kit (PE Biosystems, Foster City, Calif.), and quantitative real-time PCR (Q-PCR) was performed using SYBR green PCR Supermix in an iCycler (Bio-Rad Laboratories, Mississauga, Ontario). Each reaction contained 10 µl SYBR green Supermix, 100 nM forward and reverse primers and 1 µl cDNA. Total reaction volume was adjusted with water to 20 µl. The reactions were incubated at 50° C. for 2 min, 10 min at 95° C., followed by 45 cycles of 15 s at 95° C. and 1 min at 60° C. Subsequently, a melting curve analysis was performed with continuous fluorescence measurement. Gene expression was presented using the $2^{-\Delta\Delta CT}$ method (Livak and Schmittgen, 2001).

Example 7

Determination of Cytokine Levels in the BAL Supernatant and Lung Homogenates

The levels of IFN-γ, IL-4, IL-5, IL-10, IL-12p70, and IL-13 in the BAL fluid (BALF) and lung homogenate supernatant were measured by the Beadlyte® mouse cytokine detection kit (Upstate Biotechnology, Lake Placid, N.Y.) on a Luminex® 100IS system (Luminex Corp, Austin, Tex.) according to the manufacturer's instructions (Andersson et al., 2006). The lower limit of detection was <2 pg/ml for IL-4, IL-10, and IL-13, 5.54 pg/ml for IL-12p70, 8.97 pg/ml for IFN-γ, and 30.9 pg/ml for IL-5, respectively.

Example 8

Statistical Analysis

All parametric data are presented as mean±standard deviation (SD) for each group, and non-parametric data are presented as median (ranges). Differences between groups were analyzed by Student t test or by one-way and two-way ANOVA followed by the Tukey-Kramer multiple comparison test, when appropriate. P<0.05 was considered to be statistically significant. All statistical analyses were done using GraphPad Prism® version 4.0 (GraphPad Software, San Diego, Calif.).

Example 9

Figure 4:
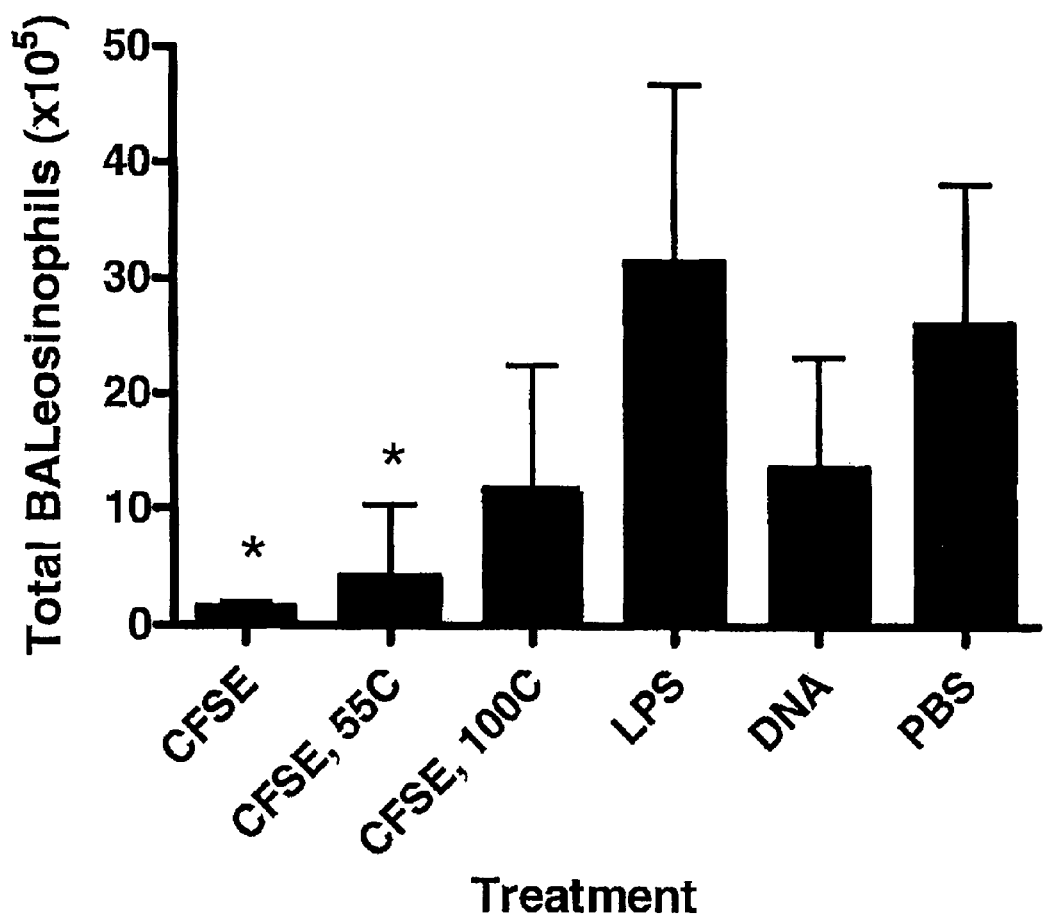
FIG. 4 is a graph showing inhibition of airway eosinophilia in OVA sensitized mice by different *F. tularensis* LVS components. Mice were sensitized i.p. with OVA on days 0 and 14 and intranasally treated with different LVS components in 50 μl of PBS on day 24, as indicated: 150 μg CFSE (CFSE), 150 μg CFSE heated to 55° C. (CFSE 55 C), 150 μg CFSE heated to 100° C. (CFSE 100 C), 20 μg LPS (LPS), 10 μg DNA (DNA) or PBS alone. Mice were i.n. challenged with OVA on day 31. Cells in the bronchoalveolar lavage (BAL) were collected at 7 days after OVA challenge, and total eosinophils in BAL fluid were enumerated on cytospin preparations. Each bar represents the mean total number of eosinophils in BAL fluid ±SD (n=5). The data presented are representative of 1 of at least 2 separate experiments with similar results. *p<0.05 compared to PBS-treated group.

*F. tularensis* LVS Immunization Inhibits Airway Eosinophilia and Pulmonary Pathology in Ova-Sensitized Mice Groups of OVA-sensitized C57BL/6 mice (as indicated in Example 3) were immunized with varying numbers of live LVS or PBS, by either i.n. or i.d. route on day 0. The mice were i.n. challenged with OVA on day 21 and sacrificed 7 days later. OVA challenge of PBS-treated sensitized mice induced the infiltration of large numbers of eosinophils and mononuclear cells, as well as some neutrophils into the lung, while the cohort group that was challenged with PBS contained only a few alveolar macrophages in their BAL fluid (data not shown). In contrast, intranasal immunization of OVA-sensitized mice with either 100 or 200 cfu of live *F. tularensis* LVS prior to the OVA challenge significantly inhibited eosinophil influx in the BAL fluid (up to 95%) without affecting the recruitment of macrophages, as compared to PBS-treated mice (FIG. 1). Similarly, i.d. immunization of OVA-sensitized mice with $2\times10^5$ cfu of live *F. tularensis* LVS prior to OVA challenge resulted in a 60% inhibition of total eosinophil number in the BAL (FIG. 1). These results demonstrated that both intranasal and, to a lesser degree, intradermal LVS immunization prevented the development of allergic airway eosinophilia (hallmark of airway allergic disease) in mice that were prior sensitized to OVA.

Example 10

*F. tularensis* CSFE Immunization Inhibits Airway Eosinophilia and Pulmonary Pathology in Ova-Sensitized Mice We next examined whether LVS infection of the host was essential for the above observed suppression of allergic airway eosinophilia. In this series of experiments, groups of OVA-sensitized C57BL/6 mice were i.n. treated with either 150 μg CSFE (total protein basis) or PBS 7 days before i.n. OVA challenge. As shown in FIGS. 2*a* and 2*b*, CFSE administration effectively inhibited the eosinophilia in the BAL fluid at a magnitude comparable to that induced by live LVS inoculation (FIG. 1), resulting in approximately a 99% decrease in airway eosinophilia at day 3 and nearly 90% at day 7 following the i.n. OVA challenge. Histological examination of lung sections showed that OVA challenge induced dramatic perivascular and peribronchial infiltration of various types of inflammatory cells in PBS-treated, OVA-sensitized mice, and CFSE treatment noticeably reduced the overall intensity of the cellular infiltration and pulmonary pathology (FIG. 3). Similar inhibitory effects by CFSE on the airway eosinophilia and associated pulmonary pathology in response to OVA challenge were also observed in Balb/c mice (data not shown). In addition, i.n. administration of $10^7$ cfu equivalent heat-killed LVS (HK-LVS) also resulted in inhibition of pulmonary eosinophilia (~60%), although the effect was not as strong and consistent as CFSE treatment (data not shown).

Example 11

LPS, Nucleic acids, and Heat Labile CFSE Components

Although the above experiments convincingly showed that CFSE is effective in the inhibition of airway eosinophilia in OVA-sensitized mice, and that bacterial infection of the host is not essential for the inhibitory effect of LVS, it must be noted that the CFSE used in our study was nevertheless a crude preparation and could potentially contain other bacterial components (such as LPS and DNA) in addition to bacterial proteins. In this regard, recent studies have shown that earlier childhood exposure to bacterial LPS reduces the risk of developing allergic airway diseases (Douwes et al., 2004) and treatment of mice with *E. coli* LPS or bacterial DNA suppresses the development of airway hyperreactivity in the mouse model of asthma (Kline et al., 2002, Kline et al., 1998, Rodriguez et al., 2003). For this reason, an additional experiment was performed to determine the potential role of the LPS or bacterial DNA in *F. tularensis*-mediated inhibition of airway eosinophilia in OVA-sensitized mice. Groups of OVA-sensitized C57BL/6 mice were i.n. treated with either LPS (20 µg) or DNA (10 µg) purified from *F. tularensis* LVS, or with one of the two heat-treated CFSE preparations, at 7 days prior to the i.n. OVA challenge. As shown in FIG. 4, neither LPS nor DNA purified from LVS, at the indicated concentrations, had any significant effect on the inhibition of airway eosinophilia in this model. On the other hand, treatment with CFSE significantly reduced the number of eosinophils in the BAL. However, prior heating of CFSE at 100° C. for 30 min, but not at 55° C. for 60 min, significantly abolished the inhibitory effect of CFSE ($p<0.05$). Collectively, these results suggest that a heat-sensitive component(s) in CFSE, other than LPS or DNA, is the likely active component in effecting the suppression of airway eosinophilia.

Example 12

Figure 5:
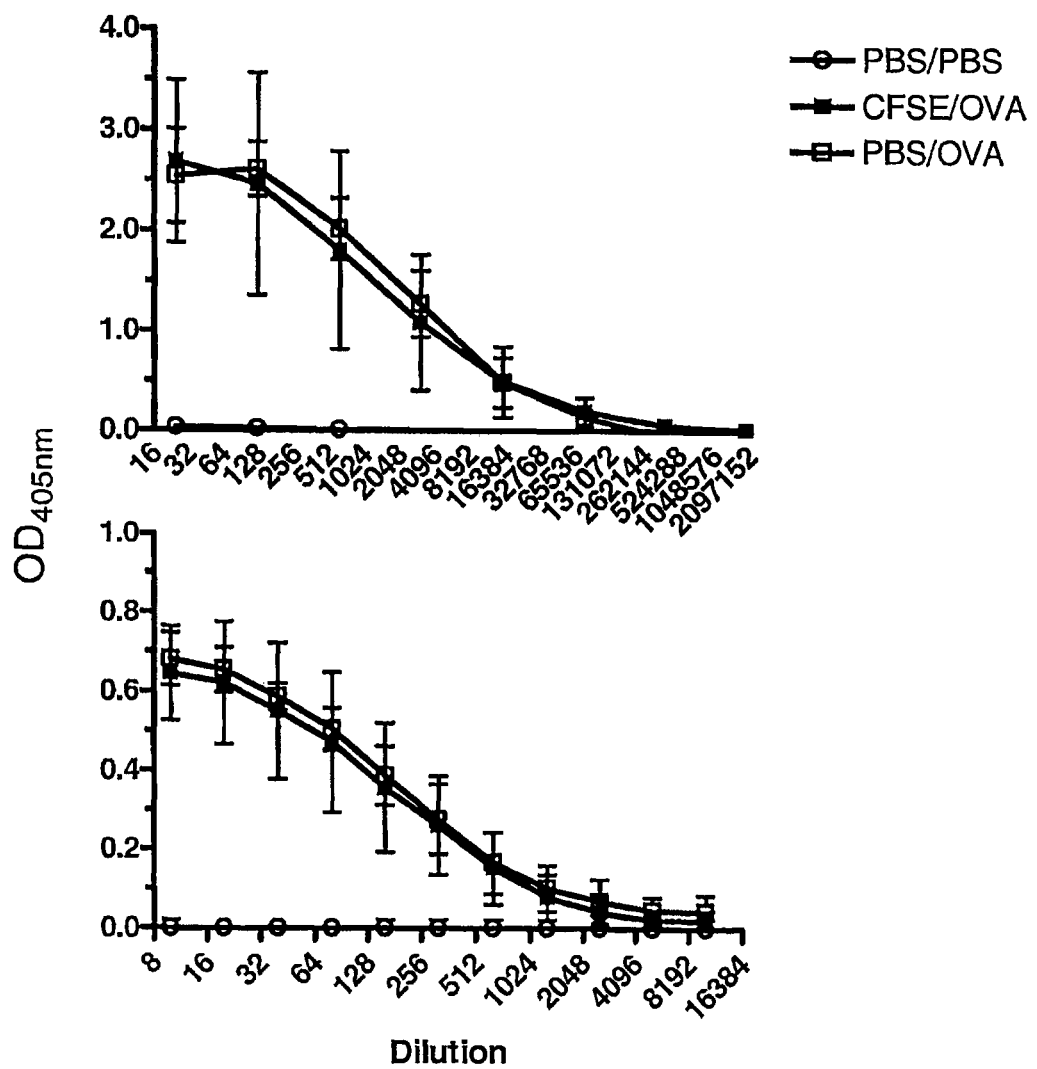
FIG. 5 shows OVA-specific serum IgG1 (top panel) and IgE (bottom panel) levels in mice sensitized with OVA but not challenged (open circles) and in OVA-sensitized mice treated with CFSE (closed squares) or PBS (open squares) prior to OVA challenge. Groups of 5 mice were euthanized seven days after i.n. OVA challenge, and serum was collected. The OVA-specific IgE, and IgG1 levels were measured using ELISA. Each data point represents the mean OD±SD of five mice in each group. Data are representative of 1 of at least 2 independent experiments.

Inhibition of Airway Eosinophilia by CFSE does not Involve Immunoglobulin Isotype Switch from IgG1 and IgE Isotypes As the first step towards understanding the potential mechanism(s) of LVS-mediated inhibition of airway eosinophilia, the effect of treatment of OVA-sensitized C57BL/6 mice with CFSE on the serum levels of Th2-dependent production of antigen-specific IgG1 and IgE was examined and compared. In agreement with published report (Ennis et al., 2005, Erb et al., 1998, Sayers et al., 2004, Smit et al., 2003), OVA-sensitization alone (no treatment post sensitization and no challenge; PBS/PBS group) induced only background levels of OVA-specific IgG1 (FIG. 5, top panel) and IgE (FIG. 5, bottom panel). Intranasal OVA challenge induced a significant increase in serum OVA-specific IgG1 and IgE in sensitized mice ($p<0.001$). However, treatment of sensitized mice with CFSE showed no effect on either the serum OVA-specific IgE or IgG1 levels, as compared with PBS treatment ($p>0.05$)(FIG. 5).

Example 13

Figure 6:
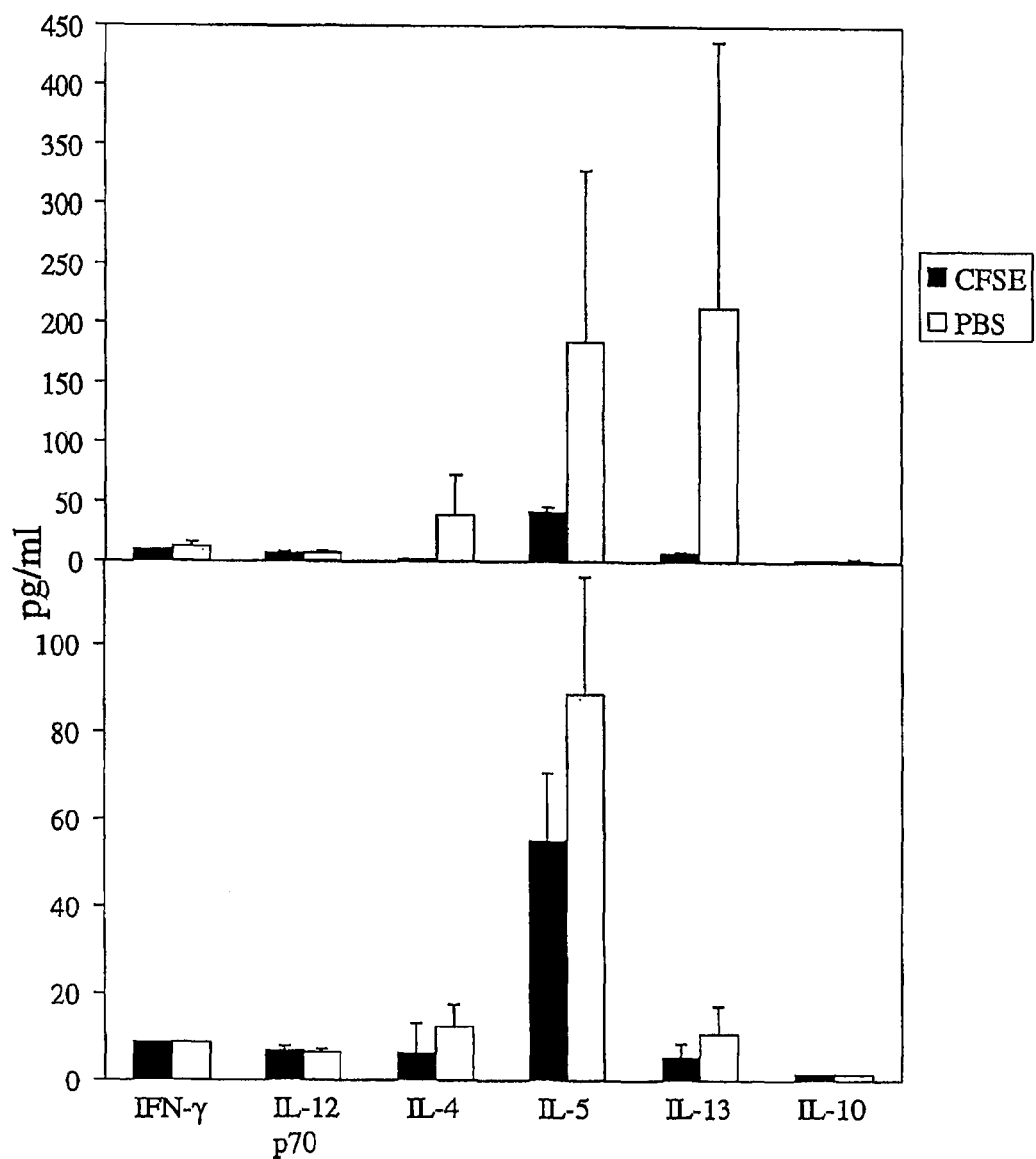
FIG. 6 is a graph showing the effect of CFSE treatment on cytokine levels in the BAL (top panel) and lung homogenates (bottom panel) in OVA-sensitized mice following i.n. OVA challenge. CFSE treatment significantly inhibits the levels of Th2 cytokines IL-4, IL-5 and IL-13 in the BAL fluid and, to a lesser extent, in the lung homogenate supernatants. Mice were sensitized and treated as described in FIGS. 2a and 2b and were euthanized three days after i.n. OVA challenge. The levels of indicated cytokines in BAL and in the lung homogenate supernatants were measured on a Luminex™ 100IS system using the Beadlyte™ mouse cytokine detection kit. Each bar represents the mean indicated cytokine (μg/ml)±SD (n=4). The data are representative of 2-3 independent experiments.

Inhibition of Airway Eosinophilia by CFSE is Associated with Local Suppression of Th2 Immune Response It is now well-established that airway eosinophilia and inflammatory responses associated with allergic asthma are regulated by multiple proinflammatory mediators, and Th2 cytokines play crucial roles in the pathogenesis of allergic asthma (Lazaar and Panettieri, 2004, Lukacs, 2001). To examine the effect of CFSE treatment on the local cytokine profiles, the mRNA expression of IFN-γ and IL-12p70 (Th1-associated), IL-4, IL-5, and IL-13 (Th2-associated), and IL-10 (regulatory/suppressor function associated) were determined in the lung and trachaeobronchial lymph nodes (TBLNs), and their corresponding protein levels were assayed in the BAL and lung homogenate supernatants from mice sacrificed at day 3 after i.n. OVA challenge. Compared to PBS treatment, CFSE treatment moderately reduced the IL-5 and IL-13 mRNA expression in the TBLNs and slightly increased the IFN-γ and IL-12p40 mRNA expression (Table 1). Similarly, CFSE treatment showed substantial inhibitory effect on the expression of IL-5 and IL-13 mRNA in the lungs but the effect on mRNA expression of other cytokines was less discernable (Table 1). Consistent with the mRNA expression pattern, CFSE treatment also significantly reduced the levels of IL-4, IL-5 and IL-13 in the BAL and, to a lesser degree, in the lung homogenates, in response to the i.n. OVA challenge (FIG. 6).

TABLE 1

Relative cytokine mRNA expression in lung and tracheobronchial lymph nodes (TBLNs) in OVA-sensitized and CFSE-treated mice after i.n. OVA challenge

| Cytokine | TBLNs | Lung |
| --- | --- | --- |
| IL-4 | 0.96 (0.62-1.48) | 0.36 (0.27-0.50) |
| IL-5 | 0.57 (0.45-0.72) | 0.19 (0.12-0.30) |
| IL-13 | 0.59 (0.37-0.96) | 0.17 (0.11-0.24) |
| IL-10 | 0.70 (0.56-0.88) | 1.53 (2.58-2.58) |
| IFN-γ | 1.27 (0.71-2.28) | 0.57 (0.41-0.81) |
| IL-12p35 | 0.72 (0.49-1.07) | 0.37 (0.18-0.76) |
| IL-12p40 | 1.60 (0.80-3.23) | 2.51 (1.48-4.26) |

Figure 2A:
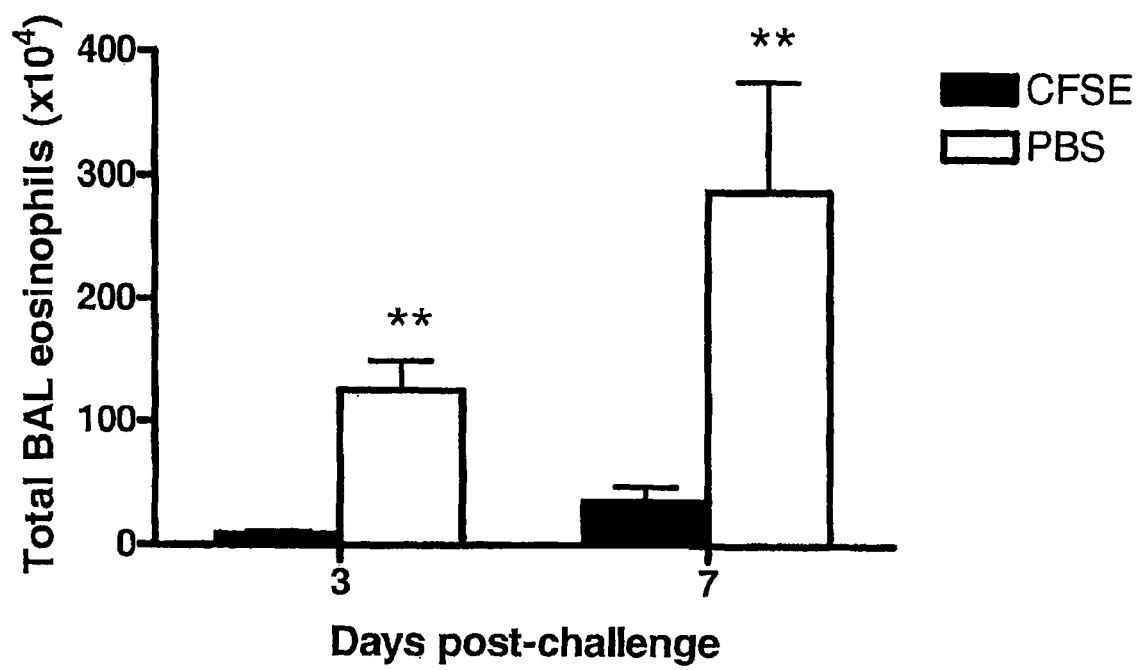
FIG. 2a is a graph showing inhibition of airway eosinophilia in OVA sensitized mice by intranasal treatment with *F. tularensis* LVS cell-free sonicate extracts (CFSE). Mice were sensitized i.p. with OVA/alum on days 0 and 14. Sensitized mice were i.n. treated with CFSE (150 μg total protein basis) or PBS on day 29 and i.n. challenged with OVA on day 36. Cells in the bronchoalveolar lavage (BAL) were collected at 3 or 7 days after OVA challenge and different cell types were enumerated on cytospin preparations. Each bar represents the mean total numbers of eosinophils in the BAL fluid ±SD (n=5). The data presented are representative of 1 of at least 2 separate experiments with similar results. **p <0.01 compared to PBS-treated group.
Figure 2B:
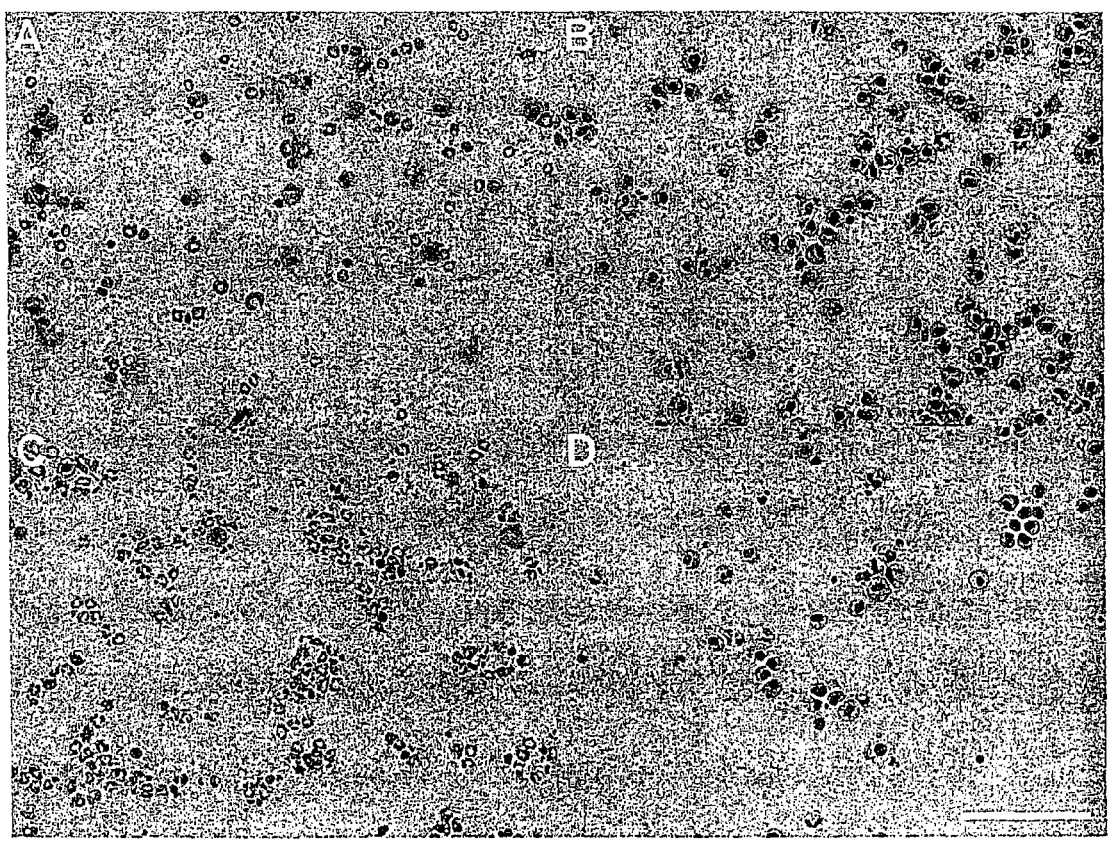
FIG. 2b shows BAL cells from OVA-sensitized mice that were treated with PBS (A and C) or CFSE (B and D), and sacrificed on day 3 (A and B) or 7 (C and D) after i.n. challenge with OVA as indicated in the FIG. 2a legend. The majority of BAL cells from CFSE-treated mice (B and D) are large alveolar macrophages with a foamy cytoplasm, whereas the BAL cells from PBS-treated mice (A and C) consist of mainly eosinophils with a donut- or horseshoe-shaped nucleus and a pink (color not seen in the black and white figure) granular cytoplasm. HemaStat-3 staining, bar=100 μm.
Figure 3:
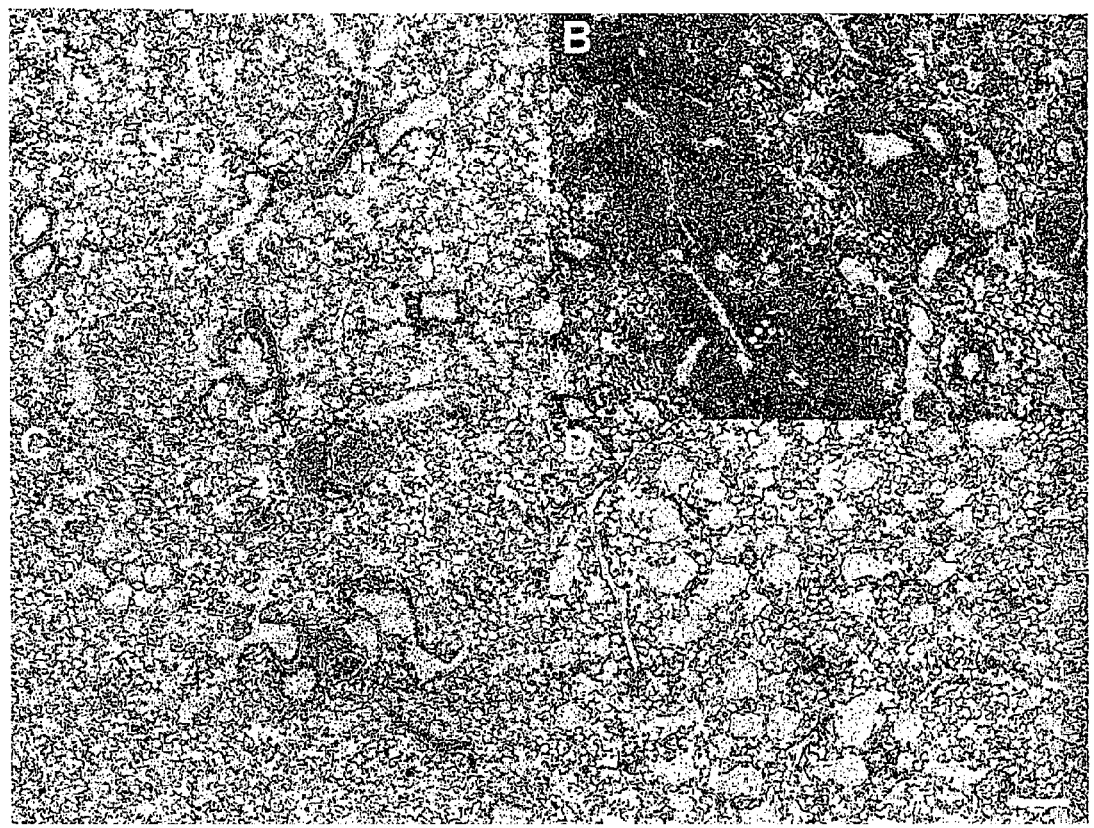
FIG. 3 shows representative lung sections from a normal control mouse (A; mice not OVA-sensitized nor treated, prior to OVA challenge) and from OVA-sensitized mice treated with PBS (B), live LVS (C) or CFSE (D) 7 days before i.n. OVA challenge. The mice were sensitized and treated as described in FIGS. 2a and 2b and killed 7 days after the OVA challenge. Their lungs were fixed and tissue sections were stained with haematoxylin and eosin (HE). Compared with the control mouse (A), note the severe pulmonary inflammation in the areas adjacent to various sized airways in OVA-sensitized mice which were PBS-treated prior to OVA challenge (B), whereas the inflammation was relatively minor in the lungs of mice treated with LVS immunization (C) or with CFSE (D). Bar=200 μm.

Mice were sensitized and treated as described in FIG. 2 and were euthanized three days after i.n. OVA challenge. The lungs and TBLNs were collected for RNA extraction. Relative levels of cytokine mRNA expression were determined by real-time PCR analysis. Mouse β2 microglobulin RNA was measured and used to calculate relative expression using the formula Rel Exp=$2-(\Delta\Delta CT)$. Results shown are the average of relative expression values determined using cDNA from 5 CFSE-treated mice with ranges in parentheses in relation to the corresponding expression levels in 5 PBS-treated mice.

Example 14

Obtaining Fractions from CFSE

The CFSE obtained as described in Example 2 was separated into different fractions and sub-fractions using a combination of ammonium sulfate precipitation followed by ion exchange column chromatography. Any similar methods known in the prior art for separation of soluble proteins would also be suitable for obtaining sub-fractions from CFSE. Briefly, to 20 ml of CFSE (ca 100 mg total protein), ammonium sulfate powder was added to 50% saturation. After a 60-minute incubation at 4° C. (with several brief periods of mixing by means of vortexing in between), the material was centrifuged (16,000×RCF, 10 minutes). The pellet from the 50% ammonium sulfate precipitated protein was dissolved in 20 ml of deionized distilled water. This solution was centrifuged once again as before, but only for 2 minutes, to remove any insoluble material, and the supernatant with the soluble proteins was collected. This supernatant was dialyzed (Spectra/Pro® dialysis tubing with molecular weight cut off of 3.5 kD; Spectrum Laboratories, Inc., Rancho Dominguez, Calif., USA) against saline (0.85% NaCl) for 48 hours at 4° C., with 3× buffer changes in between. This dialyzed solution was briefly centrifuged (16,000×RCF, 2 minutes) to remove any precipitate and the supernatant is referred to as Fraction #1 of CFSE. The supernatant obtained following the first centrifugation after 60 minutes incubation of CFSE with 50% saturated ammonium sulfate above, was collected and brought to 100% ammonium sulfate saturation (by adding more ammonium sulfate) and incubated for 1 hour at 4° C. as described above. The protein precipitated out of solution by the 100% ammonium sulfate induced precipitation from the supernate (obtained after 50% ammonium sulfate precipitation of protein from CFSE) was collected, dissolved in water and dialyzed against saline as described for Fraction #1, and was labeled as Fraction #2 from CFSE.

An aliquot of Fraction #1 (2.5 mg total protein basis, 20 mM pH 7.4 phosphate buffer) from CFSE was loaded on to a Cellufine® sulfate (Chisso Corporation, Tokyo, Japan) affinity column, and the column was washed with the phosphate buffer. The unbound proteins coming off the washing step were collected as 4 separate sub-fractions, and each was concentrated using a centrifugal filtering device (Microcon® centrifugal filter with a molecular weight cutoff of 3 kD; Millipore Corporation, Bedford, Mass., USA) as per the manufacturer's instructions. These 4 sub-fractions of the unbound proteins were labeled as unbound protein sub-fractions UBP #1, UBP #2, UBP #3 and UBP #4, respectively. These unbound protein sub-fractions, under the column loading and washing conditions would consist of anionic proteins, and the cationic proteins would remain bound to the Cellufine® sulfate. The proteins that were bound to the column were eluted with 20 mM phosphate buffer (pH 7.4) supplemented with 3 M NaCl. The eluted proteins were collected as one sub-fraction, and the sub-fraction was desalted and concentrated using a centrifugal filtering device as explained for the unbound protein sub-fractions above. The de-salted sub-fraction was centrifuged (16,000×RCF, 2 minutes) and the pellet (protein precipitated during de-salting) was re-suspended in phosphate buffer and labeled as BPP (bound protein precipitate). The supernate, comprising the solubilized (or soluble) proteins was labeled as BPS (bound protein soluble).

Figure 7:
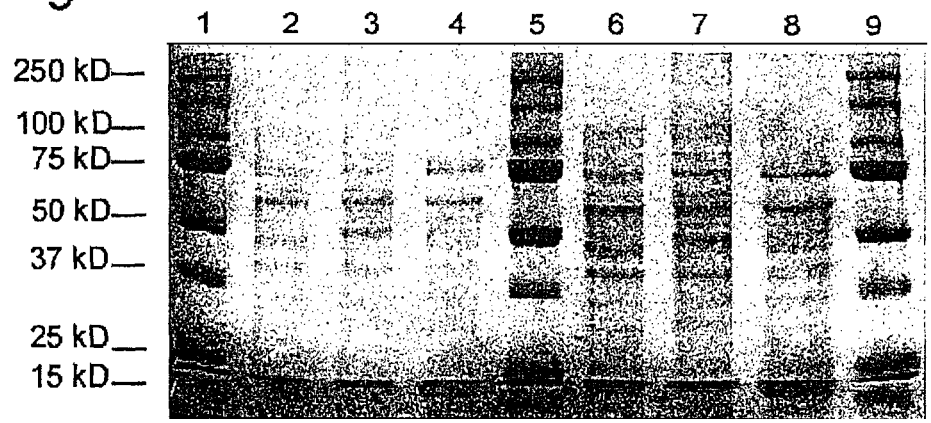
FIG. 7 shows the SDS-PAGE analyses of CFSE, and Fraction #1 and Fraction #2 of CFSE. Lanes 1, 5 and 9 are molecular weight standards. CFSE, Fraction #1 and Fraction #2 were loaded onto lanes 2 and 6, 3 and 7, and 4 and 8, respectively. The loading onto lanes 2 to 4 and 6 to 8, was 5.0 μg and 10.0 μg (total protein basis), respectively. The profiles show major differences in the protein band patterns in Fraction #1 and Fraction #2 (especially evident at the higher loading). Fraction #1 has at least 9 protein bands, at approximately 110, 85, 75, 70, 60, 50, 40, 35 and 33 kD (lane 7). The bands at approximately 110, 85, 70, and 50 kD seen in Fraction #1 (lane 7) are absent or barely visible in Fraction #2 (lane 8). The protein at ca 50 kD in Fraction #1 is especially in higher proportion compared to in CFSE.

The SDS-PAGE profile of CFSE as compared with Fraction #1 and Fraction #2 is shown in FIG. 7. The figure shows that the protein band profiles of CFSE (the original material), and Fraction #1 and Fraction #2 obtained from CFSE, are distinct from one another. The major differences in the protein band patterns in Fraction #1 and Fraction #2 are that the Fraction #1 has protein bands of approximately 110, 85, 70, and 50 kD, which are absent or barely visible in Fraction #2. The protein band at ca 50 kD in Fraction #1 is especially in higher proportion compared to that in CFSE.

Figure 8:
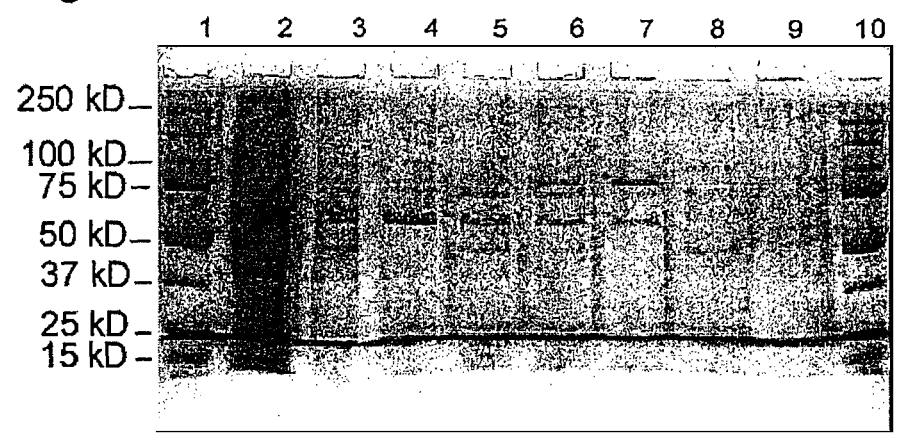
FIG. 8 shows the SDS-PAGE analyses of sub-fractions of Fraction #1 of CFSE. Lanes 1 and 10 are molecular weight standards. Lanes 2 and 3 show the protein profiles of Fraction #1 loaded at 21.4 and 2.14 μg protein, respectively. Lanes 4 to 7 are UBP #1 to UBP #4, respectively. Lanes 8 and 9 are fractions BPS and BPP, respectively. Lanes 3-9 were each loaded at 2.14 μg total protein basis, for the respective sub-fractions. The protein band profiles (patterns and intensity of the bands) seen in the sub-fractions indicate the distinct characteristics of each sub-fraction.
Figure 9:
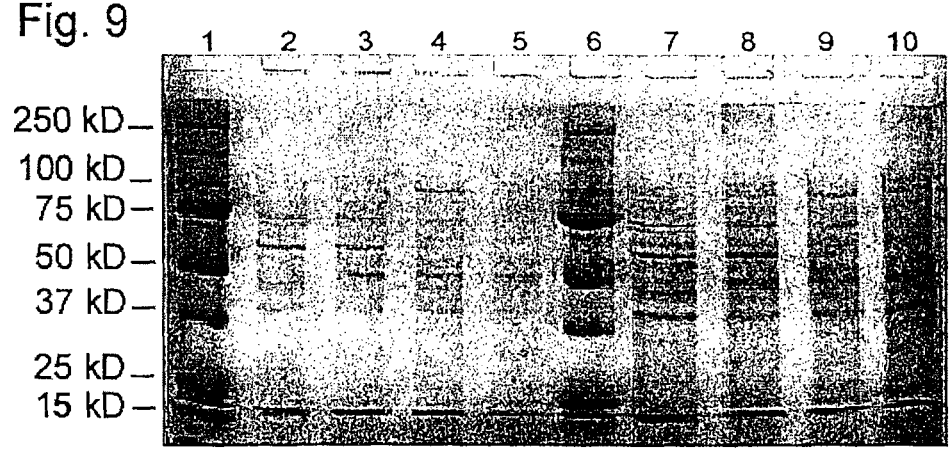
FIG. 9 shows the SDS-PAGE analyses of CFSE, Fraction #1, BPS and BPP at total protein loading of 2.5 and 5.0 μg each. Lanes 1 and 6 are molecular weight standards. Lanes 2 and 7, 3 and 8, 4 and 9, and 5 and 10 are CFSE, Fraction #1, BPS and BPP, respectively. Lanes 2-5 were loaded at 2.5 μg total protein, and lanes 7-10 at 5.0 μg total protein. The data shows that the protein band profiles of fractions BPS and BPP are similar. Fraction #1, and both BPS and BPP, have a much denser band at ca 50 kD as compared to that seen in CFSE.

The protein profiles of the Fraction #1 were compared with those of UBP #1, UBP#2, UBP #3, UBP #4, BPS and BPP, by SDS-PAGE analyses using 12.5% polyacrylamide gels. The protein band profile of Fraction #1 is distinct from those of the other sub-fractions (FIG. 8), as seen from lanes 3 versus the lanes 4-9 (the total protein loading in each of these lanes was the same, 2.14 µg). The profile of Fraction #1 in FIG. 8 is similar to that seen in FIG. 7. In UBP #1, there is one major band (based on protein stain) at ca 60 kD, and a minor one at ca 75 kD (FIG. 8, lane 4). In UBP #2, there are 3 major bands, one at 75 kD, one at ca 60 kD and one at ca 50 kD (FIG. 8, lane 5). In UBP #3 there are major bands at ca 85, 75, 60 and 50 kD (FIG. 8, lane 6). The UBP #4 sub-fraction has two major bands, one at ca 85 and another at ca 60 kD (FIG. 8, lane 7). The BPS and BPP sub-fractions each have 2 bands of comparable intensity at ca 60 and 50 kD, and BPS has one band of slightly higher intensity at ca 110 kD. Essentially the BPP and BPS sub-fractions exhibit similar protein band profiles. FIG. 8 shows that there are distinct differences in the pattern and intensity of protein bands in the different sub-fractions obtained from Fraction #1 of CFSE. The protein profiles of CFSE, Fraction #1, BPS and BPP were further compared by SDS-PAGE analyses at the higher loading of 2.5 and 5.0 µg total protein basis each, to better compare these fractions for similarities and/or differences in composition (FIG. 9). These results confirm that the protein band profiles of the fractions BPS and BPP are similar, and both these fractions have a much denser band at ca 50 kD as compared with that seen in CFSE.

Example 15

Figure 10:
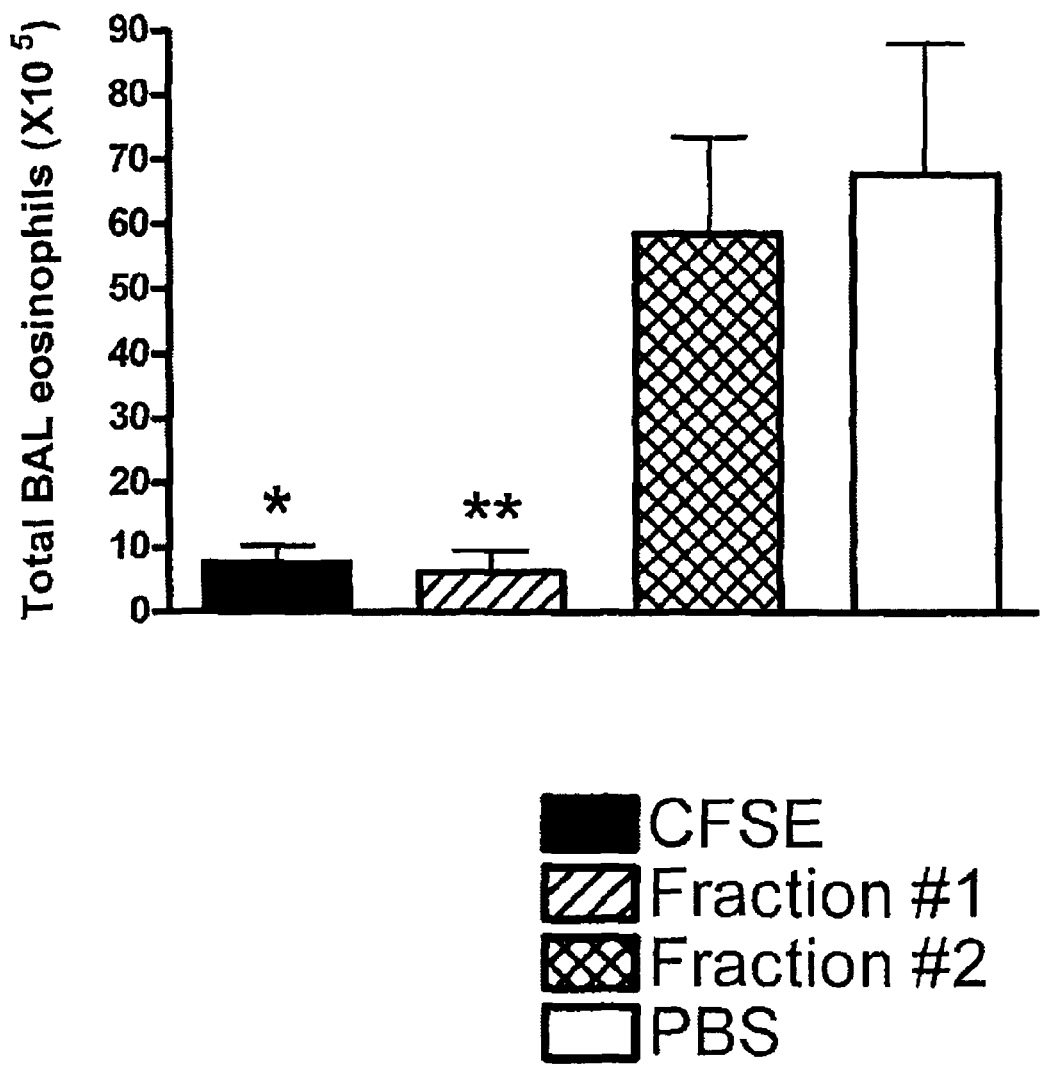
FIG. 10 shows the effect of treatment of OVA-sensitized mice with CFSE, Fraction #1 or Fraction #2 of CFSE on the inhibition of airway eosinophilia upon subsequent OVA challenge. Mice were sensitized to OVA by i.p. injection of OVA/alum at 0 and 14 days as described in Example 3. Groups of OVA-sensitized mice (n=5) were intranasally treated (as described in Example 3) with CFSE (150 μg/mouse), Fraction #1 (25 μg/mouse) or Fraction #2 (25 μg/mouse) of CFSE obtained in Example 14 (SDS-PAGE profiles shown in FIG. 7). The indicated treatment doses are based on the total protein in the CFSE or the indicated fractions. At 7 days post treatment, all mice were intranasally challenged with OVA as described in Example 3. A control group of OVA-sensitized mice was treated with PBS instead of CFSE or the fractions, prior to OVA challenge. Bronchoalveolar lavage (BAL) fluid was collected from each mouse 5 days after the OVA challenge, and the total BAL eosinophil counts were determined, all as described in Example 4. Each bar represents the mean total number of eosinophils in BAL fluid ±SEM of 5 mice per group. *p<0.05, **p<0.01 compared with the PBS-treated group. The results show that compared with the PBS treated group, the groups of mice treated with CFSE or Fraction #1 of CFSE, but not those treated with Fraction #2 of CFSE, showed significant inhibition of airway eosinophilia, a hallmark of allergic airway diseases. That is, CFSE and Fraction #1 were effective in preventing airway eosinophilia (airway allergic disease), whereas Fraction #2 was not.

Efficacy of Fraction #1 and Fraction #2 of CFSE in Inhibiting Airway Eosinophilia The infiltration of eosinophils and other inflammatory cells in the lower respiratory tract is the hallmark of human allergic airway diseases (such as asthma), and these cells play important roles in the pathogenesis of these disorders. Therefore, the potential therapeutic effect of different fractions and sub-fractions prepared from CFSE on human allergic airway diseases was evaluated in a mouse model of allergic asthma (described in Example 3), by determining the effect of the treatment on the reduction in total eosinophil counts in the bronchoalveolar lavage fluid as described in Example 4. Mice were sensitized to OVA by i.p. injection of OVA/alum at 0 and 14 days as described in Example 3. At 14 days post the last i.p. sensitization, groups of mice (n=5) were intranasally treated (as described in Example 3) with Fraction #1 or Fraction #2 of CFSE obtained in Example 14 (on the basis of 25 µg total protein in the fraction/mouse), and at 7 days post treatment, all mice were intranasally challenged with OVA as described in Example 3. Additional groups of OVA-sensitized mice were treated with either 150 µg total protein equivalent of CFSE (positive control) or PBS (negative control), instead of the fractions, prior to OVA challenge. Bronchoalveolar lavage (BAL) fluid was collected from each mouse 5 days after the OVA challenge, and the total BAL eosinophil cell counts were determined, all as described in Example 4. As seen in FIG. 10, Fraction #1 (treatment dose equivalent to 25 µg total protein) showed significant efficacy ($p<0.01$) in preventing airway eosinophilia (a hallmark of allergic airway diseases), to an extent that was comparable to that observed with CFSE (using a treatment dose equivalent to 150 pg total protein), whereas Fraction #2 (at the same dose as Fraction #1) had no effect in preventing eosinophil accumulation in the BAL (the data being similar to the PBS control)(FIG. 10).

Example 16

Efficacy of Sub-Fractions of Fraction #1 in Inhibiting Airway Eosinophilia

Figure 11:
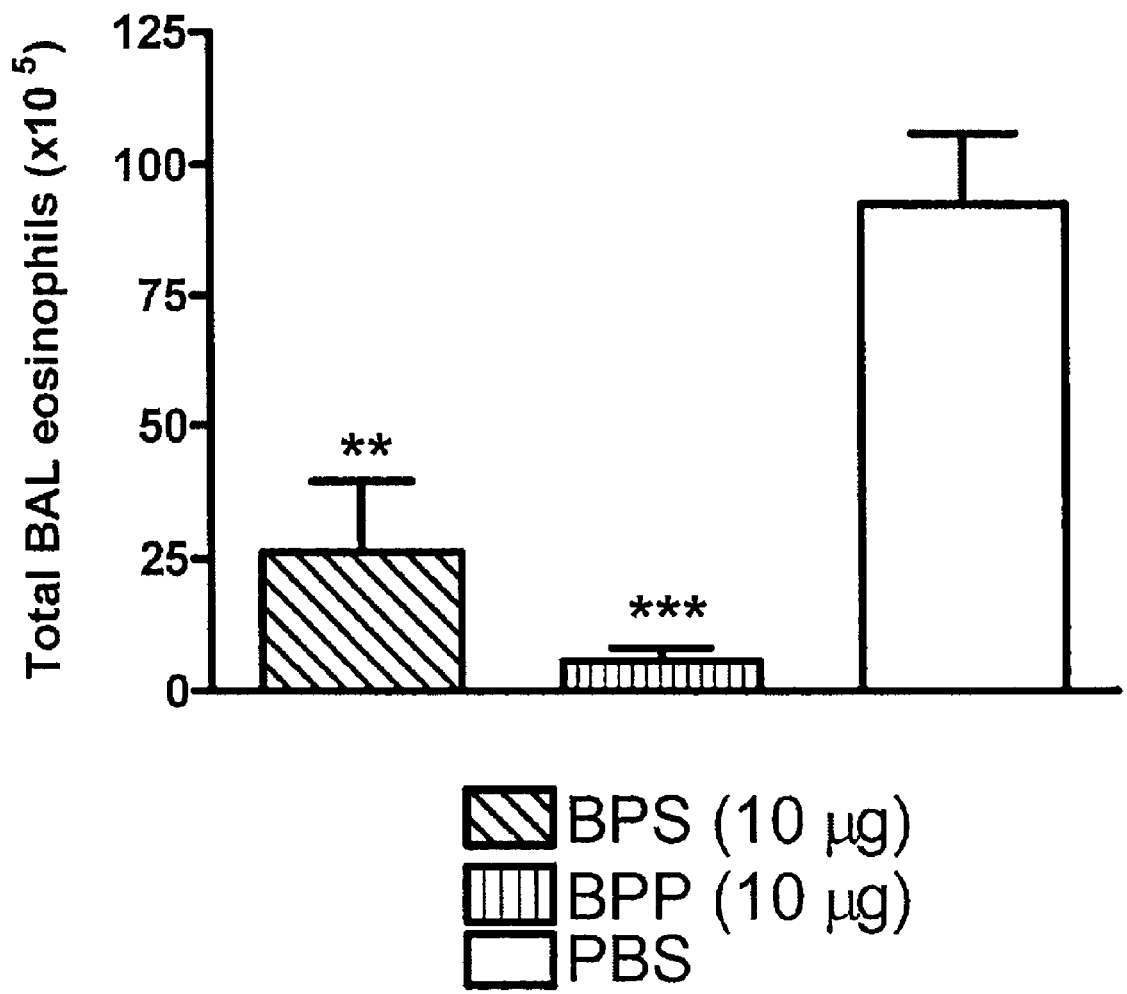
FIG. 11 shows the effect of treatment of OVA-sensitized mice with the sub-fractions BPS and BPP (obtained from Fraction #1 of CFSE) on the inhibition of airway eosinophilia upon subsequent OVA challenge. Mice were sensitized to OVA by i.p. injection of OVA/alum at 0 and 14 days as described in Example 3. Groups of mice (n=5) OVA-sensitized mice were intranasally treated (as described in Example 3) with the BPS and BPP sub-fractions of Fraction #1 obtained in Example 14, and at 7 days post treatment all mice were intranasally challenged with OVA as described in Example 3. A control group of OVA-sensitized mice was treated with PBS instead of the sub-fractions, prior to OVA challenge. Bronchoalveolar lavage (BAL) fluid was collected from each mouse 5 days after the OVA challenge, and the total BAL eosinophil counts were determined, all as described in Example 4. Each bar represents the mean total number of eosinophils in BAL fluid ±SEM of 5 mice per group. $p<<0.01$, $*p<0.001$ compared with the PBS-treated group. The results show that compared with the PBS treated group, the groups of mice treated with BPS or BPP sub-fractions obtained from Fraction #1 of CFSE showed significant inhibition of airway eosinophilia, a hallmark of allergic airway diseases, to the extent that was similar to the inhibitory effect of treatment of mice with either 150 µg CFSE or 25 µg Fraction #1 of CFSE as seen in Example 15 (FIG. 10).

Based on results in Example 15, the Fraction #1 was further sub-fractionated as described in Example 14, and the efficacy of these sub-fractions in preventing airway eosinophilia upon OVA challenge of OVA-sensitized mice was evaluated. The experiment was essentially conducted as described in Example 15, except that the OVA-sensitized mice were treated with various sub-fractions of Fraction #1 at treatment doses of 10 pg total protein per fraction (fractions as indicated in FIG. 8), prior to the OVA challenge. One control group of mice was treated with PBS only, prior to the OVA challenge. As seen in FIG. 11, compared to PBS treatment, the treatment of OVA-sensitized mice with the fractions BPS and BPP significantly inhibited the airway eosinophil response (as seen from ca 95% reduction in the total number of eosinophils in BAL fluid) in response to the subsequent intranasal OVA challenge (p<0.01 for BPS treatment and p<0.001 for BPP treatment). The prevention of airway eosinophil infiltration (a hallmark of allergic airway diseases) by BPS or BPP at the 10 µg treatment dose was comparable to that observed with treatment with 150 µg CFSE or 25 µg Fraction #1, as illustrated in Example 15 (FIG. 10). In contrast, none of the fractions UBP #1-UBP #4 had any effect in preventing infiltration of eosinophils in the lungs, as indicated by BAL fluid eosinophil counts that were similar to the PBS-treated control group (data not shown). These results indicate that the active component in CFSE comprises protein(s) bound to the Cellufine® sulfate column (as represented by BPP and BPS), which are expected to be predominantly cationic proteins (based on the column binding and elution conditions). Of the total bound protein that eluted from the Cellufine® sulfate column, two fractions were obtained, fraction BPP (proteins that precipitated upon de-salting of the eluted bound proteins) and fraction BPS (proteins that stayed in solution upon de-salting of the eluted bound proteins). However, the BPP and BPS fractions are similar in composition, based on the SDS-PAGE analyses, and in their efficacy, in preventing airway eosinophilia.

REFERENCES

All publications mentioned in this specification are indicative of the level of skill of those skilled in the art to which this invention pertains. Where permitted, all publications are herein incorporated by reference to the same extent as if each individual publication was specifically and individually indicated to be incorporated by reference.

1. Andersson, H., B. Hartmanova, R. Kuolee, P. Ryden, W. Conlan, W. Chen, and A. Sjostedt. 2006. Transcriptional profiling of host responses in mouse lungs following aerosol infection with type A *Francisella tularensis*. J Med Microbiol 55:263-271.
2. Cembrzynska-Nowak, M., E. Szklarz, A. D. Inglot, and J. A. Teodorczyk-Injeyan. 1993. Elevated release of tumor necrosis factor-alpha and interferon-gamma by bronchoalveolar leukocytes from patients with bronchial asthma. The American review of respiratory disease 147:291-295.
3. Chen, W., E. A. Havell, L. L. Moldawer, K. W. McIntyre, R. A. Chizzonite, and A. G. Harmsen. 1992. Interleukin 1: an important mediator of host resistance against *Pneumocystis carinii*. J Exp Med 176:713-718.
4. Chen, W., D. Shu, and V. S. Chadwick. 2000. Inhibition of mitogen-induced murine lymphocyte proliferation by *Helicobacter pylori* cell-free extract. J Gastroenterol Hepatol 15:1000-1006.
5. Cho, S. H., L. A. Stanciu, T. Begishivili, P. J. Bates, S. T. Holgate, and S. L. Johnston. 2002. Peripheral blood CD4+ and CD8+ T cell type 1 and type 2 cytokine production in atopic asthmatic and normal subjects. Clin Exp Allergy 32:427-433.
6. Conlan, J. W., W. Chen, H. Shen, A. Webb, and R. KuoLee. 2003. Experimental tularemia in mice challenged by aerosol or intradermally with virulent strains of *Francisella tularensis*: bacteriologic and histopathologic studies. Microb. Pathog. 34:239-248.
7. Douwes, J., G. Le Gros, P. Gibson, and N. Pearce. 2004. Can bacterial endotoxin exposure reverse atopy and atopic disease? J Allergy Clin Immunol 114:1051-1054.
8. Eigelsbach, H. T., and C. M. Downs. 1961. Prophylactic effectiveness of live and killed tularemia vaccines. I. Production of vaccine and evaluation in the white mouse and guinea pig. J Immunol 87:415-425.
9. Elias, J. A., C. G. Lee, T. Zheng, B. Ma, R. J. Homer, and Z. Zhu. 2003. New insights into the pathogenesis of asthma. J Clin Invest 111:291-297.
10. Elkins, K. L., S. C. Cowley, and C. M. Bosio. 2003. Innate and adaptive immune responses to an intracellular bacterium, *Francisella tularensis* live vaccine strain. Microbes Infect. 5:135-142.
11. Ennis, D. P., J. P. Cassidy, and B. P. Mahon. 2004. Prior *Bordetella pertussis* infection modulates allergen priming and the severity of airway pathology in a murine model of allergic asthma. Clin Exp Allergy 34:1488-1497.
12. Ennis, D. P., J. P. Cassidy, and B. P. Mahon. 2005. Whole-cell pertussis vaccine protects against *Bordetella pertussis* exacerbation of allergic asthma. Immunol Lett. 97:91-100.
13. Erb, K. J., J. W. Holloway, A. Sobeck, H. Moll, and G. Le Gros. 1998. Infection of mice with *Mycobacterium bovis*-Bacillus Calmette-Guerin (BCG) suppresses allergen-induced airway eosinophilia. J Exp Med 187:561-569.
14. Hansen, G., V. P. Yeung, G. Berry, D. T. Umetsu, and R. H. DeKruyff. 2000. Vaccination with heat-killed *Listeria* as adjuvant reverses established allergen-induced airway hyperreactivity and inflammation: role of CD8+ T cells and IL-18. J Immunol 164:223-230.
15. Jain, V. V., T. R. Busing a, K. Kitagaki, C. L. George, P. T. O'Shaughnessy, and J. N. Kline. 2003. Mucosal immunotherapy with CpG oligodeoxynucleotides reverses a murine model of chronic asthma induced by repeated antigen exposure. Am J Physiol Lung Cell Mol Physiol 285: L1137-L1146.
16. Kim, Y. S., K. S. Kwon, D. K. Kim, I. W. Choi, and H. K. Lee. 2004. Inhibition of murine allergic airway disease by *Bordetella pertussis*. Immunology 112:624-630.
17. Kline, J. N., K. Kitagaki, T. R. Busing a, and V. V. Jain. 2002. Treatment of established asthma in a murine model using CpG oligodeoxynucleotides. Am J Physiol Lung Cell Mol Physiol 283:L170-L179.
18. Kline, J. N., T. J. Waldschmidt, T. R. Busing a, J. E. Lemish, J. V. Weinstock, P. S. Thorne, and A. M. Krieg. 1998. Modulation of airway inflammation by CpG oligodeoxynucleotides in a murine model of asthma. J Immunol 160:2555-2559.
19. Larsson, P., P. C. Oyston, P. Chain, M. C. Chu, M. Duffield, H. H. Fuxelius, E. Garcia, G. Halltorp, D. Johansson, K. E. Isherwood, P. D. Karp, E. Larsson, Y. Liu, S. Michell, J. Prior, R. Prior, S. Malfatti, A. Sjostedt, K. Svensson, N. Thompson, L. Vergez, J. K. Wagg, B. W. Wren, L. E. Lindler, S. G. Andersson, M. Forsman, and R. W. Titball. 2005. The complete genome sequence of *Francisella tularensis*, the causative agent of tularemia. Nat Genet. 37:153-159.
20. Lazaar, A. L., and R. A. Panettieri. 2004. Pathogenesis and treatment of asthma: recent advances. Drug Discov. Today: Dis Mech 1:111-116.
21. Livak, K. J., and T. D. Schmittgen. 2001. Analysis of relative gene expression data using real-time quantitative PCR and the 2(-Delta Delta C(T)) Method. Methods 25:402-408.
22. Lukacs, N. W. 2001. Role of chemokines in the pathogenesis of asthma. Nat. Rev. Immunol 1:108-116.
23. Major, T., G. Wohlleben, B. Reibetanz, and K. J. Erb. 2002. Application of heat killed *Mycobacterium bovis*-BCG into the lung inhibits the development of allergen-induced Th2 responses. Vaccine 20:1532-1540.
24. Matricardi, P. M., B. Bjorksten, S. Bonini, J. Bousquet, R. Djukanovic, S. Dreborg, J. Gereda, H. J. Malling, T. Popov, E. Raz, H. Renz, and A. Wold. 2003. Microbial products in allergy prevention and therapy. Allergy 58:461-471.
25. Patel, G. B., H. Zhou, R. KuoLee, and W. Chen. 2004. Archaeosomes as adjuvants for combination vaccines. J Liposome Res 14:191-202.
26. Rodriguez, D., A. C. Keller, E. L. Faquim-Mauro, M. S. de Macedo, F. Q. Cunha, J. Lefort, B. B. Vargaftig, and M. Russo. 2003. Bacterial lipopolysaccharide signaling through Toll-like receptor 4 suppresses asthma-like responses via nitric oxide synthase 2 activity. J Immunol 171:1001-1008.
27. Sayers, I., W. Severn, C. B. Scanga, J. Hudson, G. Le Gros, and J. L. Harper. 2004. Suppression of allergic airway disease using mycobacterial lipoglycans. J Allergy Clin Immunol 114:302-309.
28. Schwarze, J., E. Hamelmann, K. L. Bradley, K. Takeda, and E. W. Gelfand. 1997. Respiratory syncytial virus infection results in airway hyperresponsiveness and enhanced airway sensitization to allergen. J Clin Invest 100:226-233.
29. Severn, W. B., G. S. Le Gros, and J. L. Harper. 2002. Vaccine comprising active agent immunogenic acyl glyceryl phosphatidylinositol manno-oligosaccharide.
30. Sjostedt, A., and D. J. Brenner. 2002. *Francisella*. Bergey's manual of systematic bacteriology. Springer-Verlag, Berlin.
31. Smit, J. J., H. Van Loveren, M. O. Hoekstra, P. A. Van der Kant, G. Folkerts, and F. P. Nijkamp. 2003. Therapeutic treatment with heat-killed *Mycobacterium vaccae* (SRL172) in a mild and severe mouse model for allergic asthma. Eur. J. Pharmacol. 470:193-199.
32. Strachan, D. P. 1989. Hay fever, hygiene, and household size. BMJ 299:1259-1260.
33. Tarnvik, A. 1989. Nature of protective immunity to *Francisella* tularensis. Rev Infect Dis 11:440-451.
34. Vinogradov, E., M. B. Perry, and J. W. Conlan. 2002. Structural analysis of *Francisella tularensis* lipopolysaccharide. Eur J Biochem 269:6112-6118.
35. Weinberger, M. 2004. Respiratory infections and asthma: current treatment strategies. Drug Discov. Today 9:831-837.
36. Wohlleben, G., J. Muller, U. Tatsch, C. Hambrecht, U. Herz, H. Renz, E. Schmitt, H. Moll, and K. J. Erb. 2003. Influenza A virus infection inhibits the efficient recruitment of Th2 cells into the airways and the development of airway eosinophilia. J Immunol 170:4601-4611.

We claim:

1. A pharmaceutical composition for administration to an animal, for the inhibition of airway eosinophilia and associated pulmonary inflammation in the animal, comprising a cell-free sonicate extract of attenuated live *Francisella tularensis* LVS cells or a protein fraction or cationic protein subfraction thereof, and a pharmaceutically acceptable excipient, diluent or carrier, wherein said protein fraction is obtained as follows:
   (i) adding ammonium sulfate powder to the cell-free sonicate extract to 50% saturation;
   (ii) centrifugation to obtain a protein pellet; and
   (iii) dissolution of the protein pellet in water; and wherein the cationic protein subfraction is obtained as follows:
   (iv) loading the dissolved protein pellet from (iii) on a cation exchange column; and
   (v) eluting the cationic protein subfraction that is bound to the column in (iv) using 3 M NaCl elution buffer;
and wherein the cell-free sonicate extract, or protein fraction, or cationic protein subfraction inhibits airway eosinophilia and associated pulmonary inflammation in the animal.

2. The composition of claim 1, wherein the composition is formulated for topical, parenteral, intradermal or respiratory administration.

3. The composition of claim 2, wherein the composition is formulated for respiratory administration.

4. The composition of claim 3, wherein respiratory administration is by intranasal administration.

5. The composition of claim 2, wherein the composition is formulated into a dosage form comprising a liquid dispersion, aerosol, gel, ointment or cream.

6. The composition of claim 2, in unit dose form containing about 150 µg total protein of cell-free sonicate extract per unit dose for respiratory administration.

7. The composition of claim 2, wherein the cell-free sonicate extract or protein fraction or cationic protein subfraction thereof comprises a heat labile component.

8. The composition of claim 2, in unit dose form containing about 25 µg total protein.

9. The composition of claim 1, wherein the composition inhibits infiltration of eosinophils in the respiratory tract.

10. The composition of claim 9, wherein the cationic protein subfraction is further fractionated to obtain a bound protein precipitate subfraction and a bound protein soluble subfraction as follows:
    (vi) the cationic protein subfraction is desalted;
    (vii) the desalted cationic protein subfraction is centrifuged to produce a pellet and a supernatant;
    (viii) the pellet from (vii) is resuspended in phosphate buffer to obtain a bound protein precipitate subfraction; and
    (ix) the supernatant from (vii) is recovered to obtain a bound protein soluble subfraction.

11. The composition of claim 10 comprising at least one of the bound protein precipitate subfraction or the bound protein soluble subfraction and wherein the composition is in a unit dose form containing about 10 µg total protein.

12. The composition of claim 10, wherein the bound protein precipitate subfraction and the bound protein soluble subfraction comprise moieties of molecular weight 50 kD or 60 kD, or both 50 kD and 60 kD.

13. A method of inhibiting the development of airway eosinophilia and associated pulmonary inflammation in an animal, comprising administering the composition of claim 1 to an animal in need thereof.

14. The method of claim 13 wherein the airway eosinophilia and associated pulmonary inflammation is caused by asthma, eosinophilic airway inflammation, airway hyperresponsiveness or allergic airway disease.

15. The method of claim 14, wherein the animal is a mammal selected from a mouse, dog, cat, sheep, goat, cow, horse, pig, non-human primate or human.

16. The method of claim 15, wherein the mammal is a human.

17. The method of claim 13, wherein the composition is administered by topical, parenteral, intradermal or respiratory routes.

18. The method of claim 17, wherein the composition is formulated into a dosage form selected from liquid dispersions, aerosols, gels, ointments or creams.

19. The method of claim 17, wherein the composition is administered in the form of a respiratory administrable pharmaceutical composition comprising cell-free sonicate extract in an amount of about 150 µg protein per unit dose.

20. The method of claim 17, wherein the composition is administered in the form of a respiratory administrable pharmaceutical composition comprising the protein fraction or the cationic protein subfraction of the cell-free sonicate extract in an amount of about 25 μg protein per unit dose.

21. The method of claim 17, wherein the composition is administered in the form of a respiratory administrable pharmaceutical composition comprising the protein fraction or the cationic protein subfraction of the cell-free sonicate extract in an amount of about 10 μg protein per unit dose.

22. The method of claim 17, wherein the cell-free sonicate extract or protein fraction or cationic protein subfraction thereof comprises a heat labile component.

23. The method of claim 13, wherein the composition inhibits infiltration of eosinophils in the respiratory tract.

24. The method of claim 13, wherein the cationic protein subfraction is further fractionated to obtain a bound protein precipitate subfraction and a bound protein soluble fraction as follows:
  (vi) the cationic protein subfraction is desalted;
  (vii) the desalted cationic protein subfraction is centrifuged to produce a pellet and a supernatant;
  (viii) the pellet from (vii) is resuspended in phosphate buffer to obtain a bound protein precipitate subfraction; and
  (ix) the supernatant from (vii) is recovered to obtain a bound protein soluble subfraction.

25. The method of claim 24, wherein the composition comprises at least one of the bound protein precipitate subfraction or the bound protein soluble subfraction and the composition is administered in the form of a respiratory administrable pharmaceutical composition comprising an amount of about 10 μg protein.

26. The method of claim 25, wherein the respiratory administrable route is an intranasal route.

27. The method of claim 24, wherein the bound protein precipitate subfraction and the bound protein soluble subfraction comprise moieties of molecular weight 50 kD or 60 kD, or both 50 kD and 60 kD.

* * * * *